(12) United States Patent
Weissman

(10) Patent No.: US 6,685,473 B2
(45) Date of Patent: Feb. 3, 2004

(54) IMPLANTS AND MODULAR COMPONENTS FOR ASSEMBLY OF DENTURES AND BRIDGES

(76) Inventor: Bernard Weissman, 225 E. 48th St., New York, NY (US) 10017

( * ) Notice: Subject to any disclaimer, the term of this patent is extended or adjusted under 35 U.S.C. 154(b) by 0 days.

(21) Appl. No.: 09/970,475

(22) Filed: Oct. 4, 2001

(65) Prior Publication Data

US 2002/0142265 A1 Oct. 3, 2002

Related U.S. Application Data

(60) Provisional application No. 60/237,814, filed on Oct. 4, 2000.

(51) Int. Cl.[7] .................................................. A61C 8/00
(52) U.S. Cl. ....................................... 433/173; 433/174
(58) Field of Search ................................ 433/172, 173, 433/174, 175, 176

(56) References Cited

U.S. PATENT DOCUMENTS

| 3,514,858 | A | * | 6/1970 | Silverman | 433/174 |
| 4,459,111 | A | * | 7/1984 | Valen | 433/176 |
| 4,854,872 | A | * | 8/1989 | Detsch | 433/173 |
| 5,538,428 | A | * | 7/1996 | Staubli | 433/173 |
| 5,567,155 | A | * | 10/1996 | Hansen | 433/172 |
| 5,575,651 | A | * | 11/1996 | Weissman | 433/173 |

\* cited by examiner

*Primary Examiner*—John J. Wilson
(74) *Attorney, Agent, or Firm*—Paul J. Sutton; Barry G. Magidoff

(57) ABSTRACT

A chairside prosthesis includes modular components which may be assembled and adjusted to variable ridge sizes, and held together in position with self-curing hardened resin. Such modular components are secured in the bones of the mouth in a relatively short time, which may be adjusted at a later date, and which are adaptable to variations in size and shape of ridges in the bones for more comfortable use of the dentures secured on such prostheses.

13 Claims, 49 Drawing Sheets

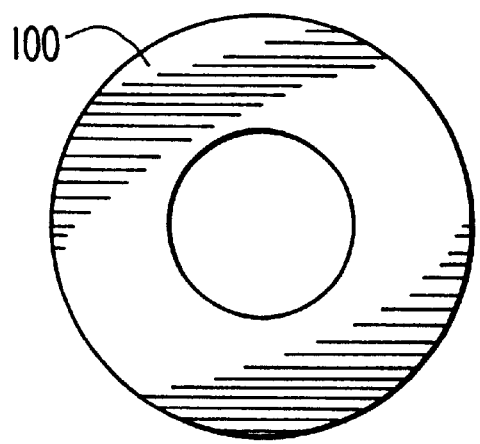
FIG. 26
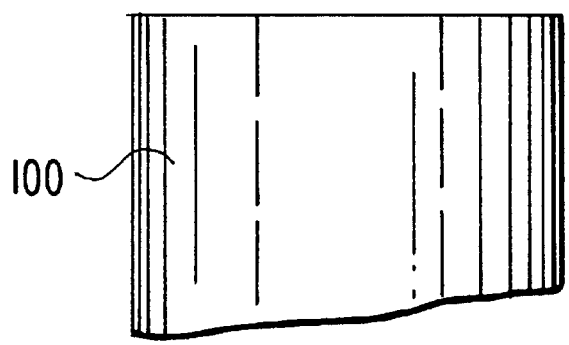
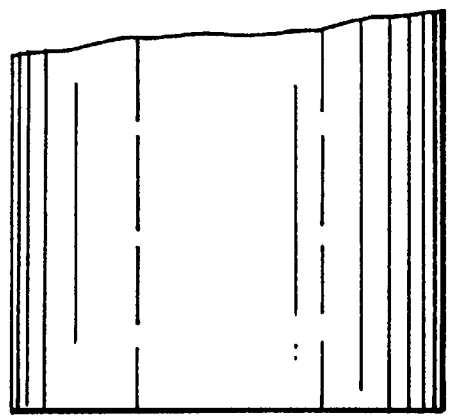
FIG. 27

FIG. 39
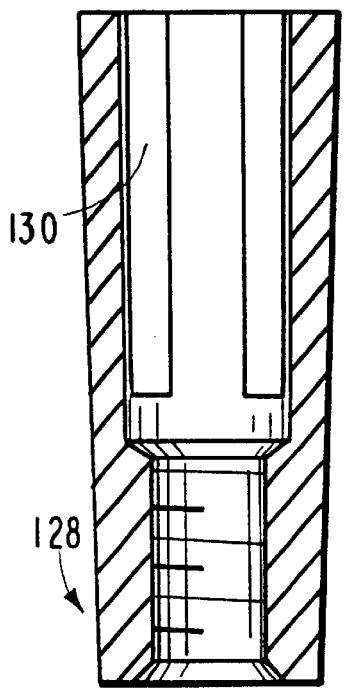
FIG. 40
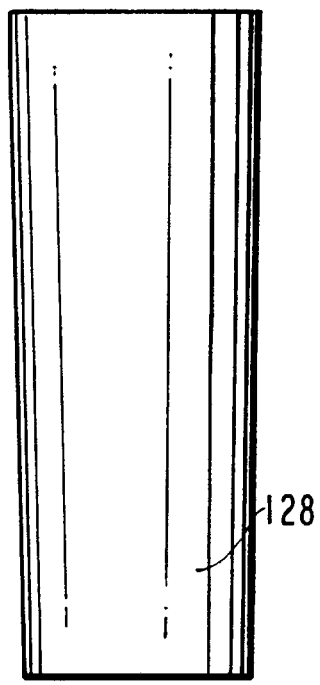
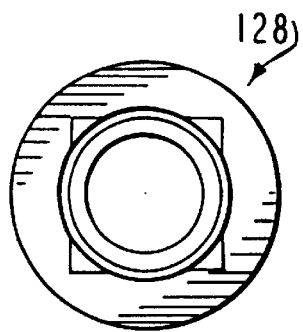
FIG. 41

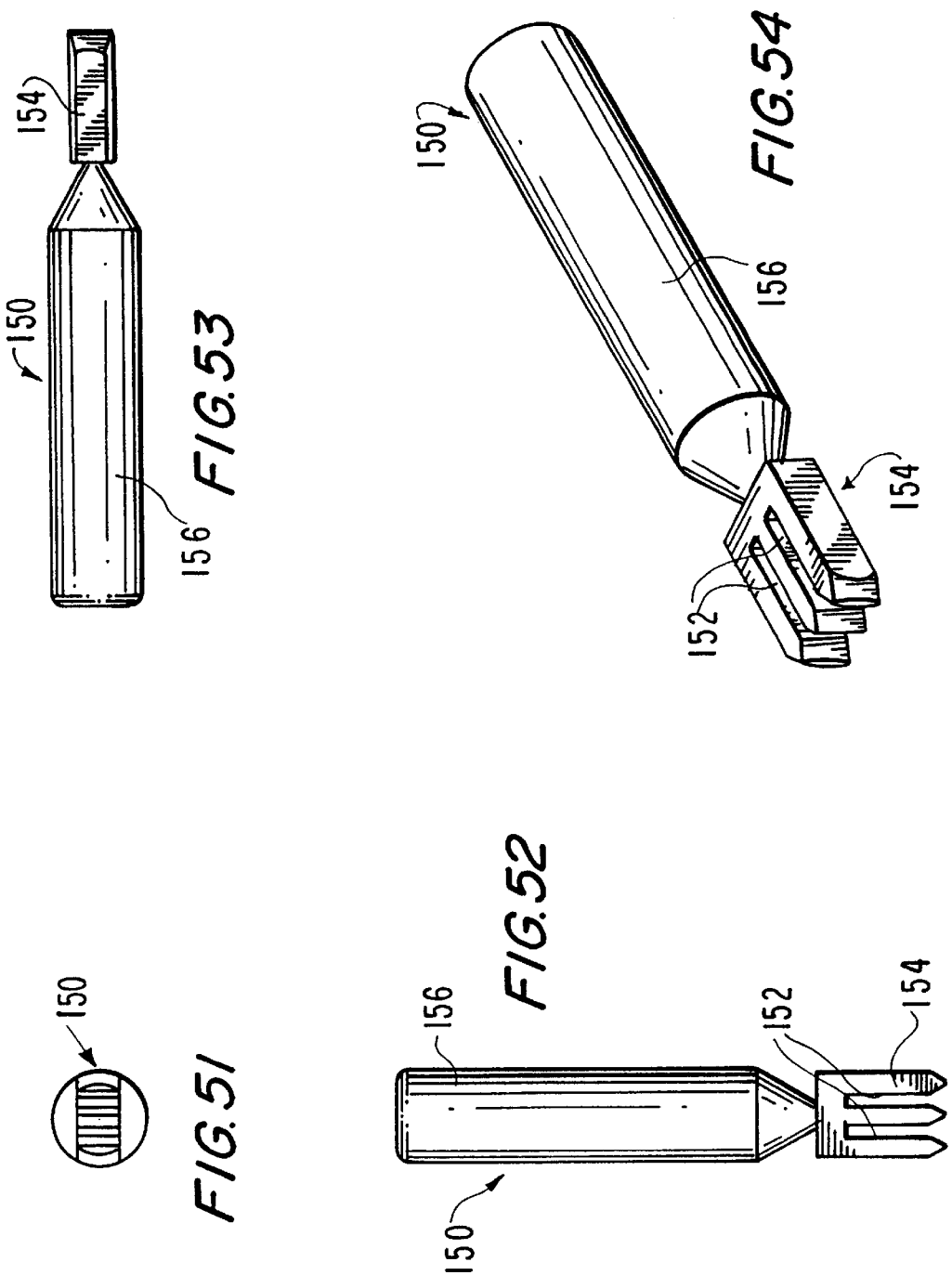

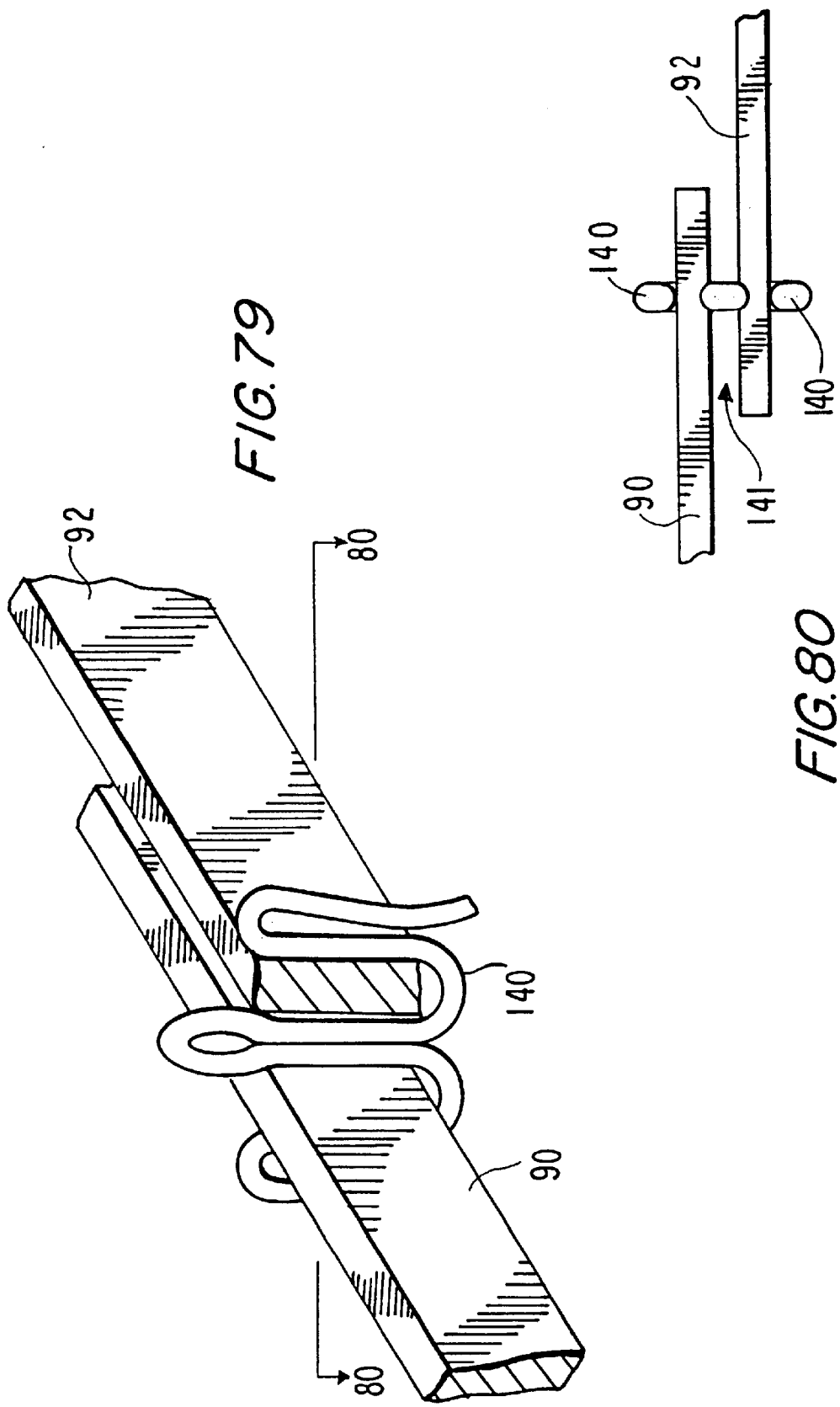

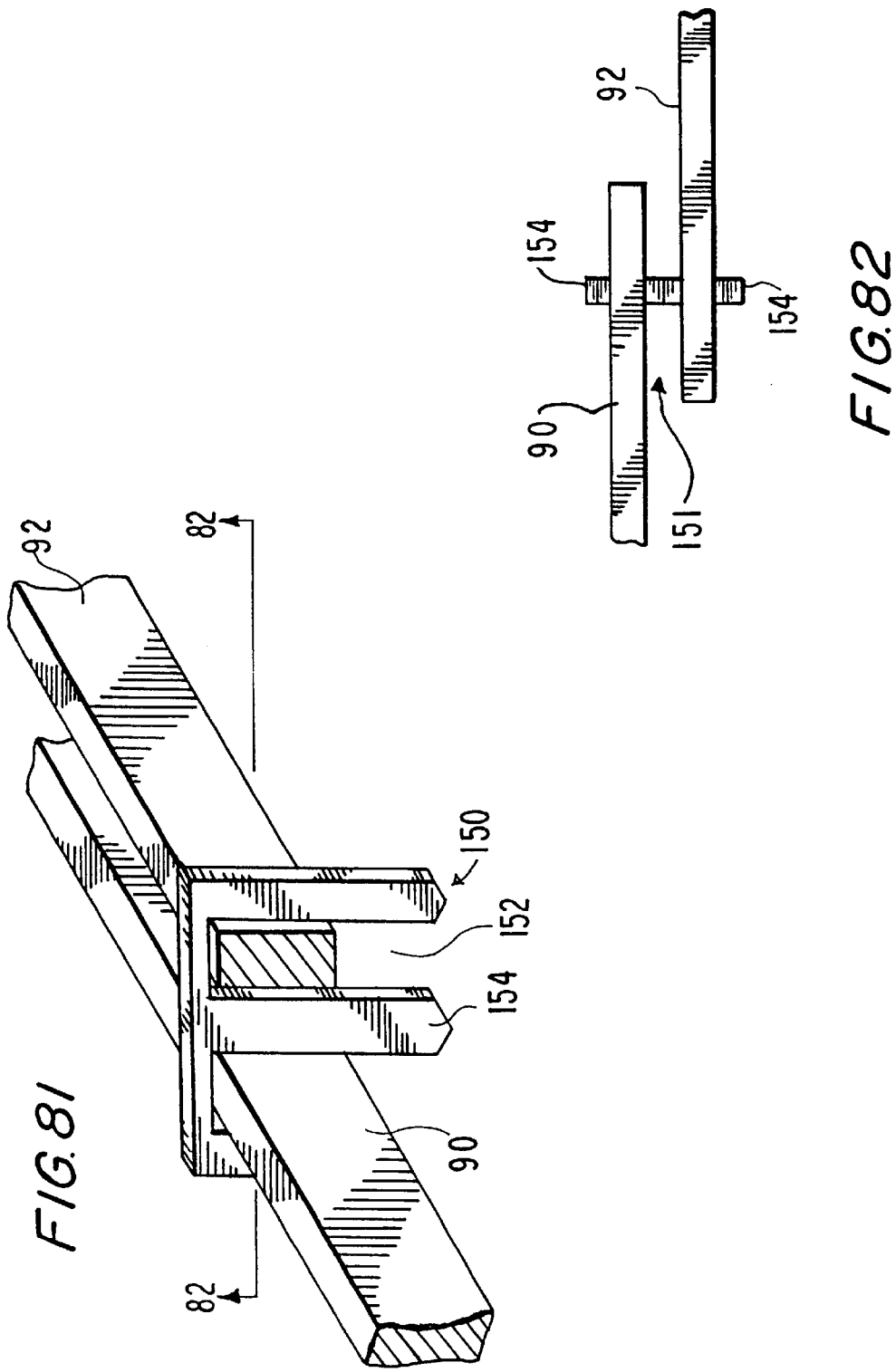

IMPLANTS AND MODULAR COMPONENTS FOR ASSEMBLY OF DENTURES AND BRIDGES

CROSS-REFERENCE TO RELATED APPLICATIONS

This invention is related to U.S. provisional patent application No. 60/237,814, filed Oct. 4, 2000, which is incorporated herein by reference.

FIELD OF THE INVENTION

The present invention relates to dental implant structures, and in particular to adjustable modular components for securing dentures and dental bridges for oral prosthetics.

BACKGROUND OF THE INVENTION

As shown in FIG. 1, prosthetic dental bridges 10 and foundations 12 for such bridges 10 are known to firmly attach dentures to hard dental tissue, such as the jawbone 14 or tooth stubs by an implanted support. In particular, the dental bridge 10 may be securely mounted to implanted screw posts 16, or other known securing mechanisms. Such foundations 12 are described, for example, in U.S. Pat. Nos. 5,575,651 and 5,788,492, each of which is incorporated herein by reference.

The foundations 12 described in the aforecited patents were considered a major advance over the earlier art, in that they avoided the original lengthy process of providing large implants, requiring many months to heal, and attached to a denture which also required great care and time. However, these earlier advances were originally intended as temporary devices for use until the permanent implants healed. It has since been recognized that permanent implants can be formed utilizing the slender screw implants of these two patents. However, these devices sometimes created problems when worn for extended periods. They lacked the capability of easy removal and replacement, and could cause irritation to the patient because of the difficulty of obtaining a proper fit to the jawbone and opposing teeth and gums, or other soft dental tissue.

Thus, a need continued to exist for a system which would permit the placement of a long-lasting dental prosthesis in a patient's mouth by chairside techniques available to the family dentist. Such a system should provide components for mounting such prosthesis which may be secured to the hard dental tissue, such as the jawbone, in a relatively short time, which may be adjusted or prophylactically cleaned or repaired at a later date, and which is readily adaptable to the natural variations in the size and shape of ridges in the bones so as to provide for more comfortable use of any dentures secured on such prostheses.

SUMMARY OF THE INVENTION

A chairside prosthesis foundation includes a plurality of screw implants, each having an intermediate platform portion and an interconnectable top distal from the screw portion, with modular components which can be connected to a group of aligned screw implants and which can be subsequently adjusted to fit a range of jaw ridge sizes and locked in position with self-curing resin. The interconnectable top permits relative ease in adjustment or removal of the screw, if necessary, and provides for the connection between the implants and the modular components. Such modular components are secured in the jaw efficiently and relatively easily, and may be adjusted at a later date, to conform to any variations in the size or shape of ridges in the jaw, rendering more comfortable to the wearer the dentures secured on such implants and modular components.

The interconnected implants and modular components are preferably further reinforced and locked together by a cured resin composition, such as a self-curing resin well known to dentists. The assembled modular components locked into place by the, e.g., hardened resin, becomes the foundation, referred to as a "splint", upon which tooth forms/synthetic teeth may be supported. The tooth forms may be created at chairside, once the splint is in place, to provide a patient with a prompt replacement of missing teeth.

BRIEF DESCRIPTION OF THE DRAWINGS

FIG. 26 illustrates a top plan view of a cap sleeve composed of silicone for insertion onto an extension member of the cap shown in FIGS. 15–18;

FIG. 27 illustrates a side cross-sectional view of the silicone cap sleeve of FIG. 26;

FIG. 39 illustrates a side cross-sectional view of an alternative embodiment of a cap key;

FIG. 40 illustrates a side plan view of the alternative embodiment of a cap key of FIG. 39;

FIG. 41 illustrates a top plan view of the alternative embodiment of a cap key of FIGS. 39–40;

FIG. 51 illustrates a bottom plan view of a spacer clip of FIG. 54;

FIG. 52 illustrates a first side plan view of the spacer clip of FIG. 54;

FIG. 53 illustrates a second side plan view of the spacer clip of FIG. 54 having a perpendicular orientation relative to the first side plan view of FIG. 53;

FIG. 54 illustrates a view of the spacer clip;

FIG. 79 illustrates a perspective view of the expander clip of FIGS. 49–50 spacing bars apart;

FIG. 80 illustrates a top cross-sectional view along lines 80—80 of the expander clip of FIGS. 49–50 spacing bars apart;

FIG. 81 illustrates a perspective view of the spacer clip of FIGS. 51–54 spacing bars apart;

FIG. 82 illustrates a bottom cross-sectional view along lines 82—82 of the spacer clip of FIGS. 51–54 spacing bars apart;

DETAILED DESCRIPTION OF THE PREFERRED EMBODIMENTS

Figure 1:
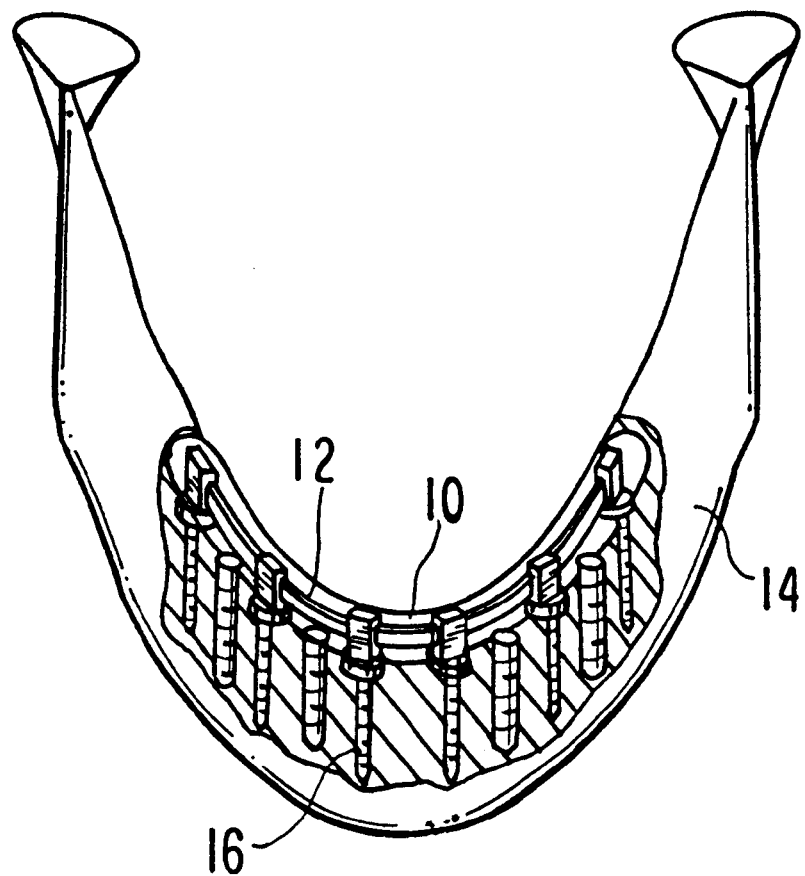
FIG. 1 illustrates dental prostheses in the prior art.
Figure 2:
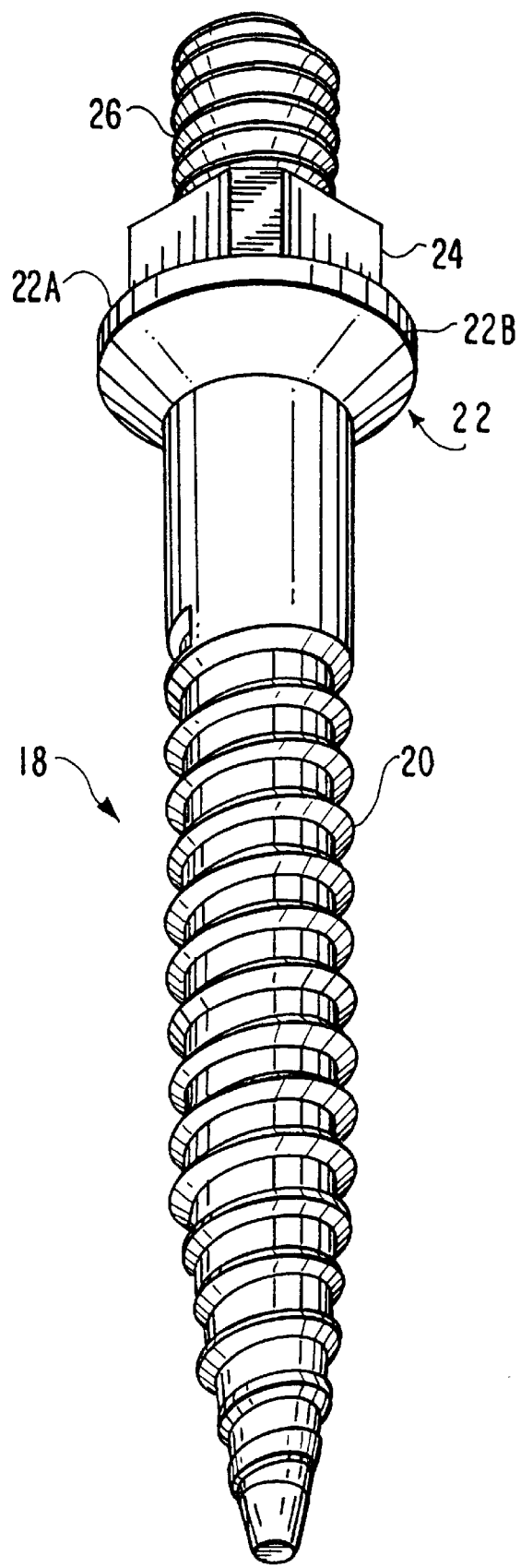
FIG. 2 illustrates a perspective view of a engineer's drawing of an implant screw with various advantageous features.
Figure 83:
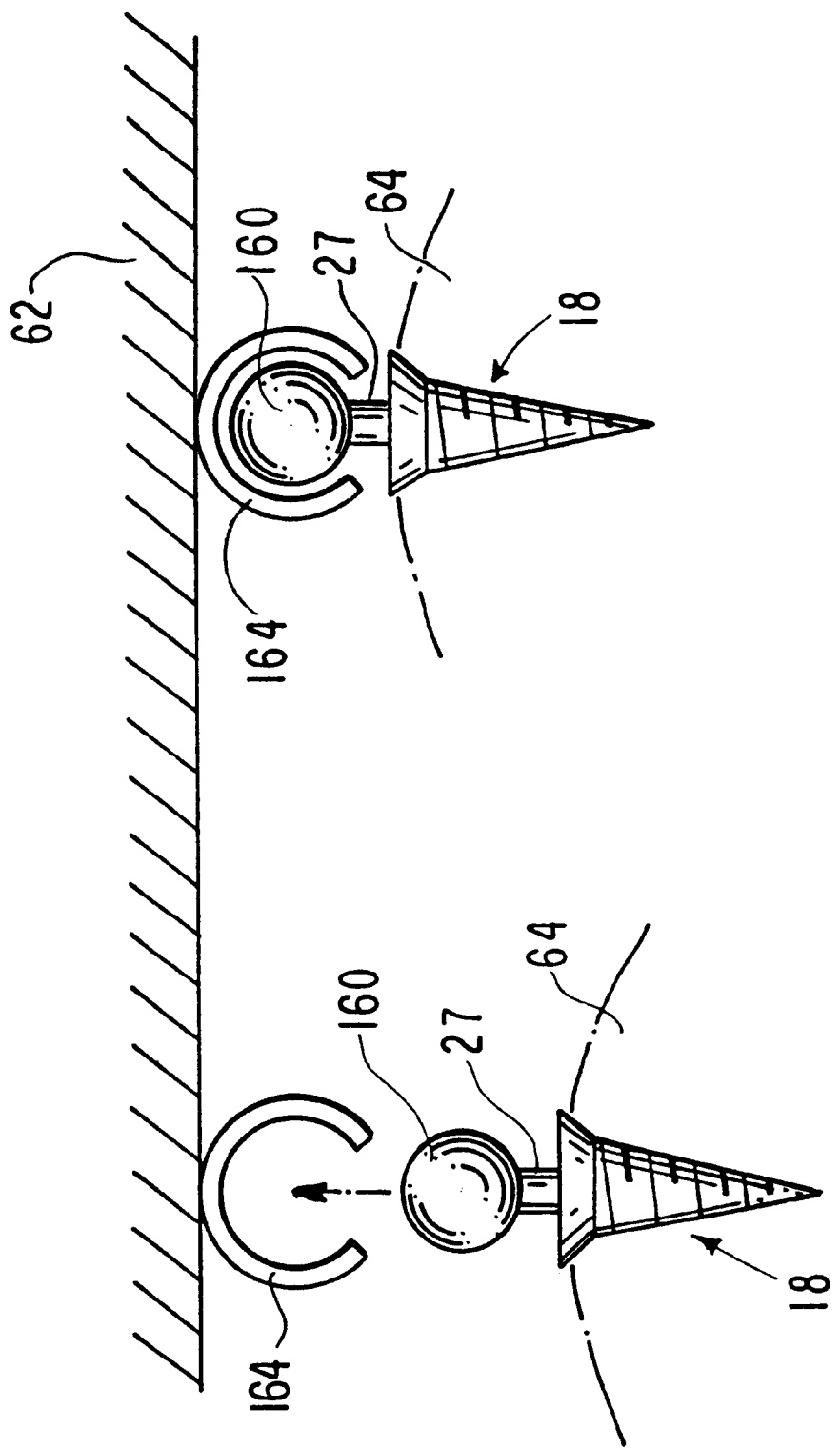
FIG. 83 illustrates a side plan view of the ball-and-socket arrangement for use with the ball cap of FIG. 75.

As described herein, the various modular components shown in FIGS. 2–83 are fabricated from, for example, titanium, stainless steel, and/or any other suitable dental implant material which can withstand functional loads and support crowns, bridge segments, or the complete replacement of teeth with tooth forms/synthetic teeth/artificial teeth.

As shown specifically in FIGS. 2 through 5, and in context elsewhere, the implant screw 18 has, at one end, a relatively long self-tapping threaded shaft 20. In use, an opening is made through any soft dental tissue, e.g., gums, overlying the jawbone, and the implant screw 18 is screwed into the hard dental tissue. The implant screw 18 has various advantageous features, such as a flange 20, functioning as an implant platform, having a flat surface 22A on a first side adjacent to which modular components are positioned and supported, and having a tapered smooth portion 22B on a second side facing the dental tissue from which the threaded shaft 20 extends. The threads preferably do not extend the full length of the shaft 20, such that a substantially smooth, unthreaded portion is preferably present immediately adjacent the tapered portion 22B In addition, this embodiment of the implant screw 18 includes a driving portion 24 which, in this example, is a flat polygonal extension, having a rectangular longitudinal cross-section. The driving portion 24 is adapted to engage a tool, such as a socket wrench bit, which may be manually or mechanically driven, such as by a dental drill, to turn the screw 18 in a selected rotational direction to secure or remove the screw 18 from the hard dental tissue, in a manner known in the art. The screw 18 can thus be anchored in the ridge portion of e.g., the jawbone in a self-threading manner. It is understood that the driving portion 24 need not be in the specific shape shown, and is preferably polygonal in lateral cross-section, such as rectangular, hexagonal, star-shaped, etc. to engage compatible tools known in the art.

The implant screw 18 also includes at the second longitudinal end, a prosthesis connecting member 26 for attaching the modular prosthesis components thereto. In the preferred embodiment of FIGS. 2–5, the prosthesis connecting member 26 is externally threaded, as shown most clearly in FIG. 2, for receiving an internally threaded cap 27; an embodiment of a cap is shown in FIGS. 15–18, for removably mounting the cap 27, to the prosthesis connecting member 26.

Figure 24:
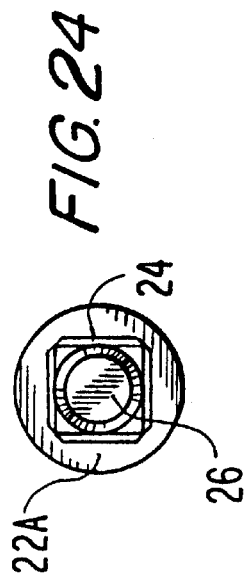
FIG. 24 illustrates a top plan views of the implant screw of FIG. 2.
Figure 25:
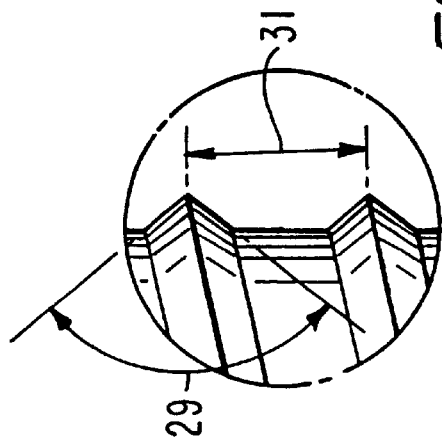
FIG. 25 illustrates a close-up side plan view of a portion of the threaded shaft of the implant screws of FIGS. 2–5.

Referring to FIG. 24, a top view of an implant screw 18 having a cap connected thereto illustrates the flat first side 22A of the flange 22, from which extends the polygonal-shaped driving portion 24. In addition, as shown in FIG. 25, the threaded shaft 20 of the implant screw 18 has a predetermined angular aspect 29 of the threads, such as a 90° orientation between successive surfaces of the thread, as well as a predefined spacing 31 between threads, with the angular aspect 29 and spacing 31 being selected for facilitating self-tapping and insertion of the insert screw 18 into hard dental tissue, such as a jawbone.

Figure 12:
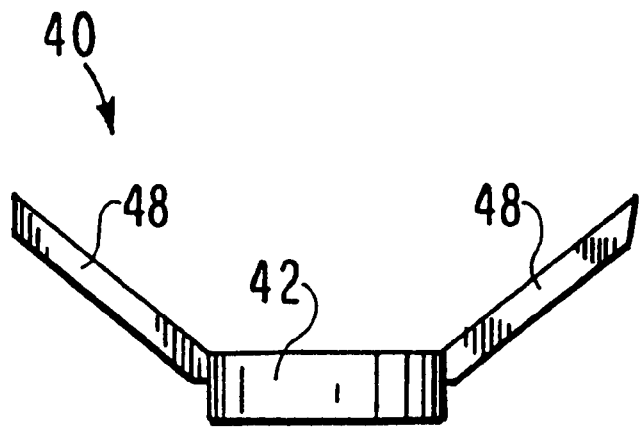
FIG. 12 illustrates a side plan view of the angular implant platform of FIG. 11.
Figure 13:
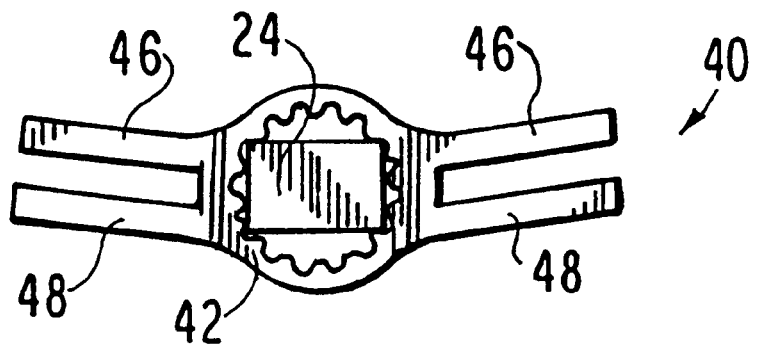
FIG. 13 illustrates a top plan view of the angular implant platform of FIG. 11.
Figure 14:
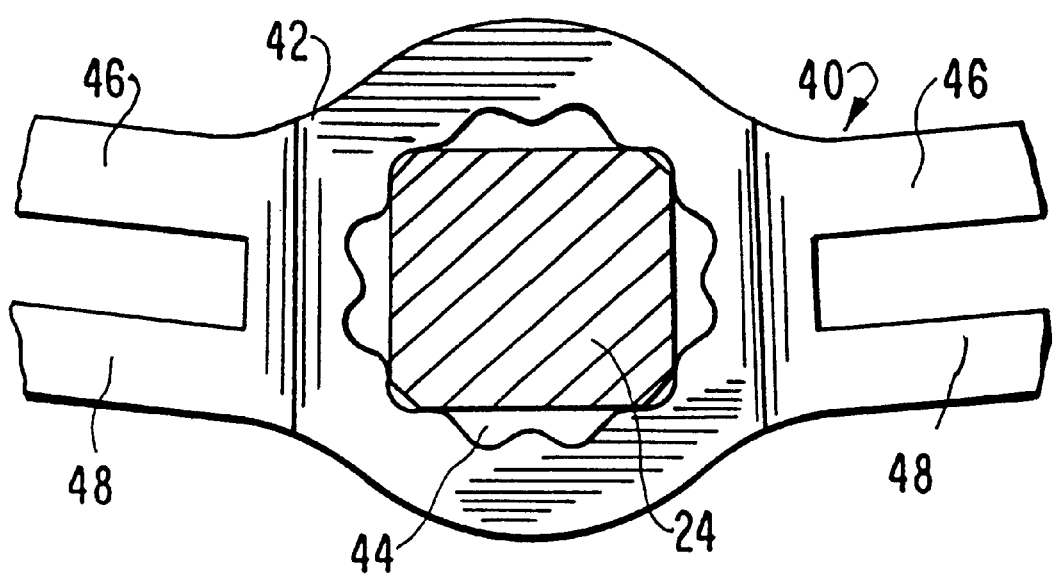
FIG. 14 illustrates a close-up of the top plan view of the angular implant platform shown in FIG. 13 with a driving portion of the implant screw positioned in the central aperture of the angular implant platform of FIG. 11.
Figure 19:
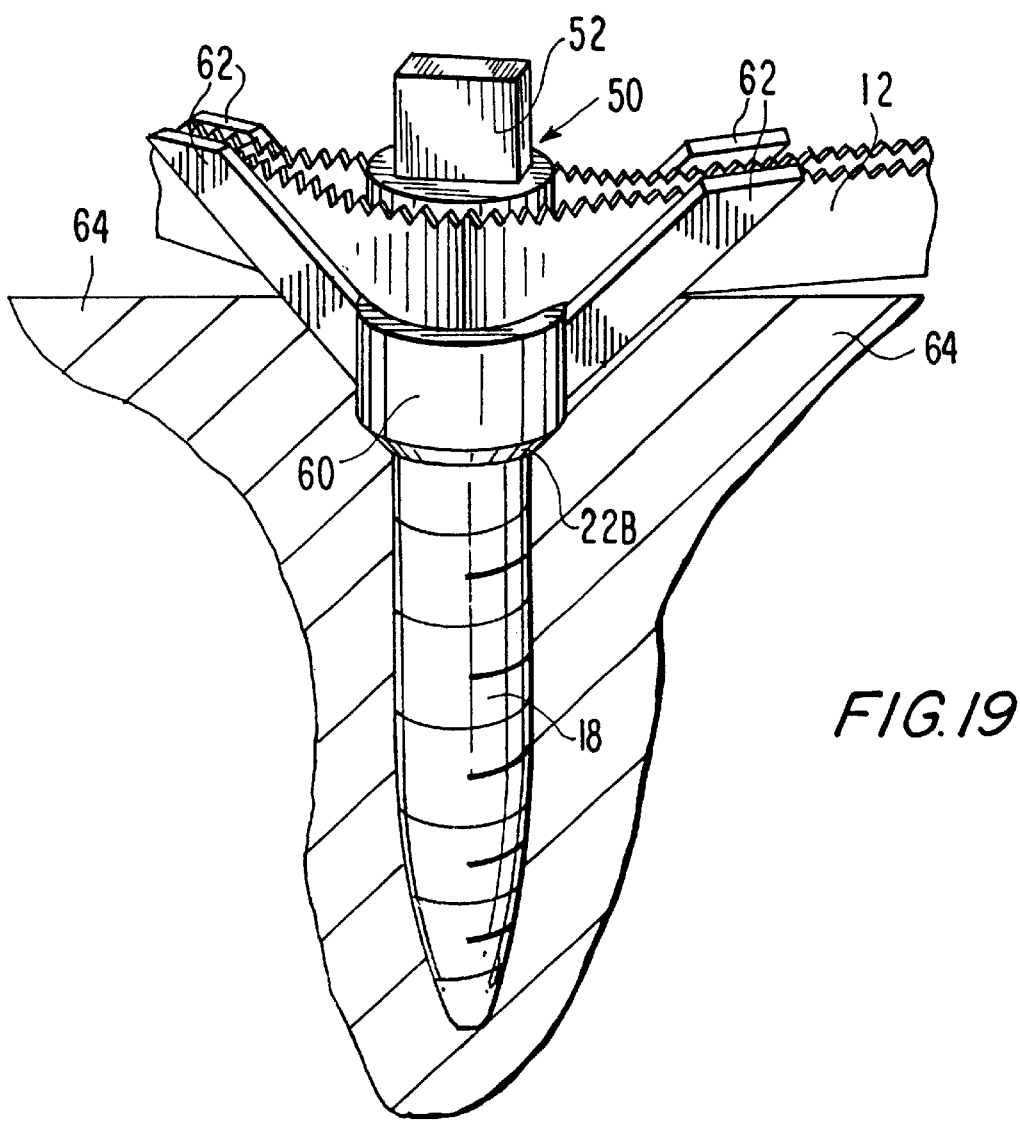
FIG. 19 illustrates a winged implant platform and a cap mounted on an implant screw and securing a bridge component.

As shown in FIGS. 14 and 19, the modular component 40, shown in greater detail in FIGS. 11–13, and FIGS. 6–10, mates with the polygonal driving portion 24 and an end surface 40a preferably rests on the implant platform surface 22A, and the tapered smooth portion 22B of the flange 22 rests against the tissue 64. Therefore, the modular component 60 disposed on the implant screw 18 and the implant platform 20 thereof is prevented from contacting the tissue, and so the modular component 60 cannot injure the tissue 64.

Figure 3:
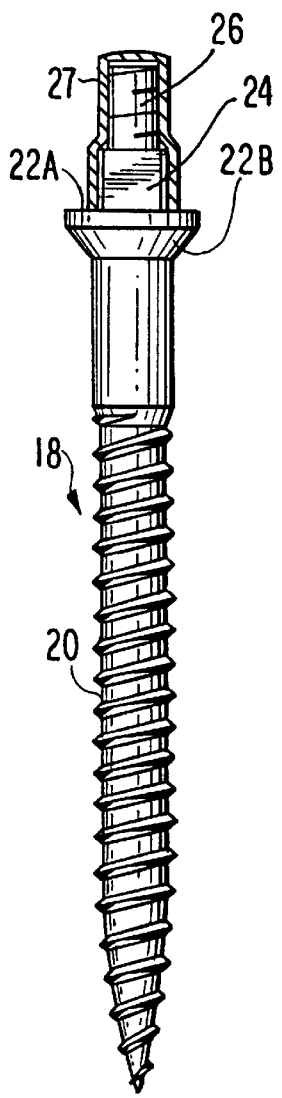
FIGS. 3–5 illustrate side views of the implant screw of FIG. 2 having a cap affixed to a prosthesis connecting member of the implant screw, and having variations in size and shape.
Figure 4:
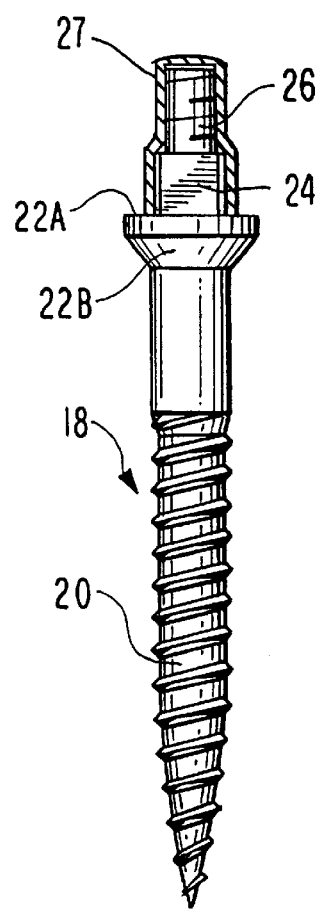
Figure 5:
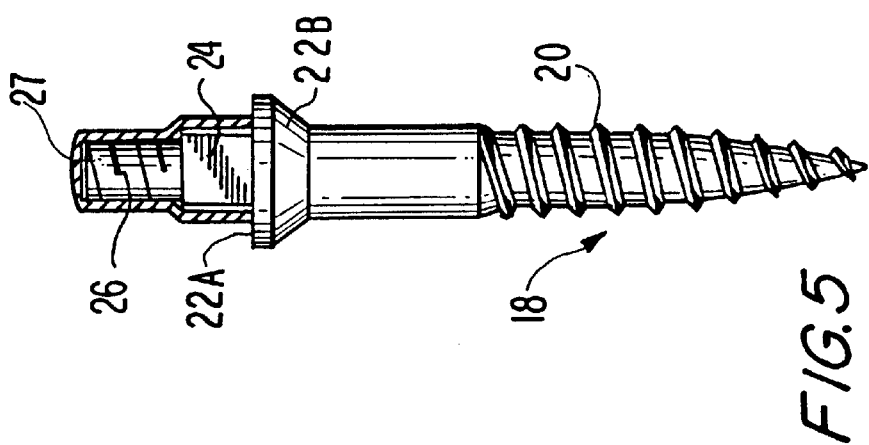

The prosthesis connecting member 26 engages a cap 27, such as shown in FIGS. 3–5, and as described herein and shown at least in FIGS. 15–18, which in turn locks e.g., the modular component 40, in place.

The present invention is a modular system for providing a dental prosthesis which is supported by screws tapped directly into hard, dental matter, such as the jawbone 14 or teeth stubs. The screw 18 comprises a threaded shaft 20, preferably having a self-tapping thread along most of its length, for screwing directly into the hard dental matter of a tooth stub or jawbone. Extending longitudinally from the threaded shaft 20 is a tapered flange 22 having a tapered portion 22B extending directly from the threaded shaft 20 and a relatively flat platform 22A distal from the threaded shaft 20, for the purpose of providing a foundation and a stop for the prosthesis resting upon and supported by the threaded screws. Preferably the taper on the flange 22 is in the range of from about 10° to about 80°, and most preferably from about 20° to about 70°, from the longitudinal, for providing a smooth interface with the soft tissue 64 surrounding the upper portion of the threaded shaft 20, as shown in FIG. 19.

Extending longitudinally from the flange platform 22A, and distal from the threaded shaft 20, is a driving portion 24, preferably having a polygonal or uneven, curvilinear cross-section. The driving portion 24 is rigidly connected, preferably to the platform 22A. Extending longitudinally from the driving portion 24 is a prosthesis connecting portion 26 which is preferably threaded. The prosthesis connecting portion 26 is preferably a threaded cylindrical shaft which can be threadably connected to a cap 27 shown in FIGS. 3–5. The diameter of the prosthesis connecting portion 26 is smaller than the cross-sectional dimension of the driving portion 24 in order to permit connection of the driving portion 24 to a drive tool, for placing the implant. The prosthesis to be mounted to the screws 18 is held in place thereon by the caps 27 on each implant screw 18. When it is desired to remove for repairing or modifying the prosthesis or for permitting prophylactic treatment during the life of the prosthesis, the caps are removed and the prosthesis merely lifted off from the screw implants. An indexing member, such as the extension units 28 and 40, as shown in FIGS. 6–14 and 19, respectively, is placed over the driving portion 24 and rests upon the screw platform 22A. The indexing member provides the first part of a modular system which is ultimately supported by a plurality of threaded screws 18.

Figure 20:
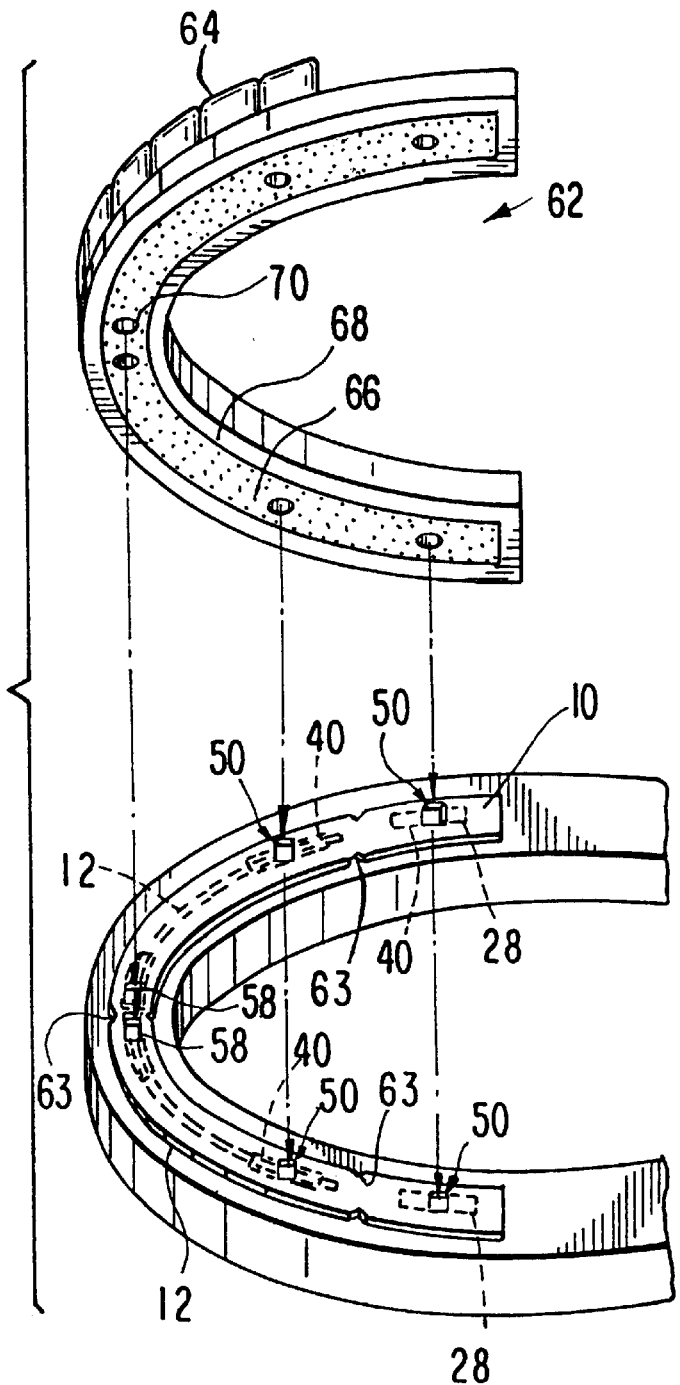
FIG. 20 illustrates an exploded perspective view of a prosthesis mounted on the bone by the modular components, and a denture having an undercut cavity in which resin is disposed for mounting the denture to the prosthesis.
Figure 21:
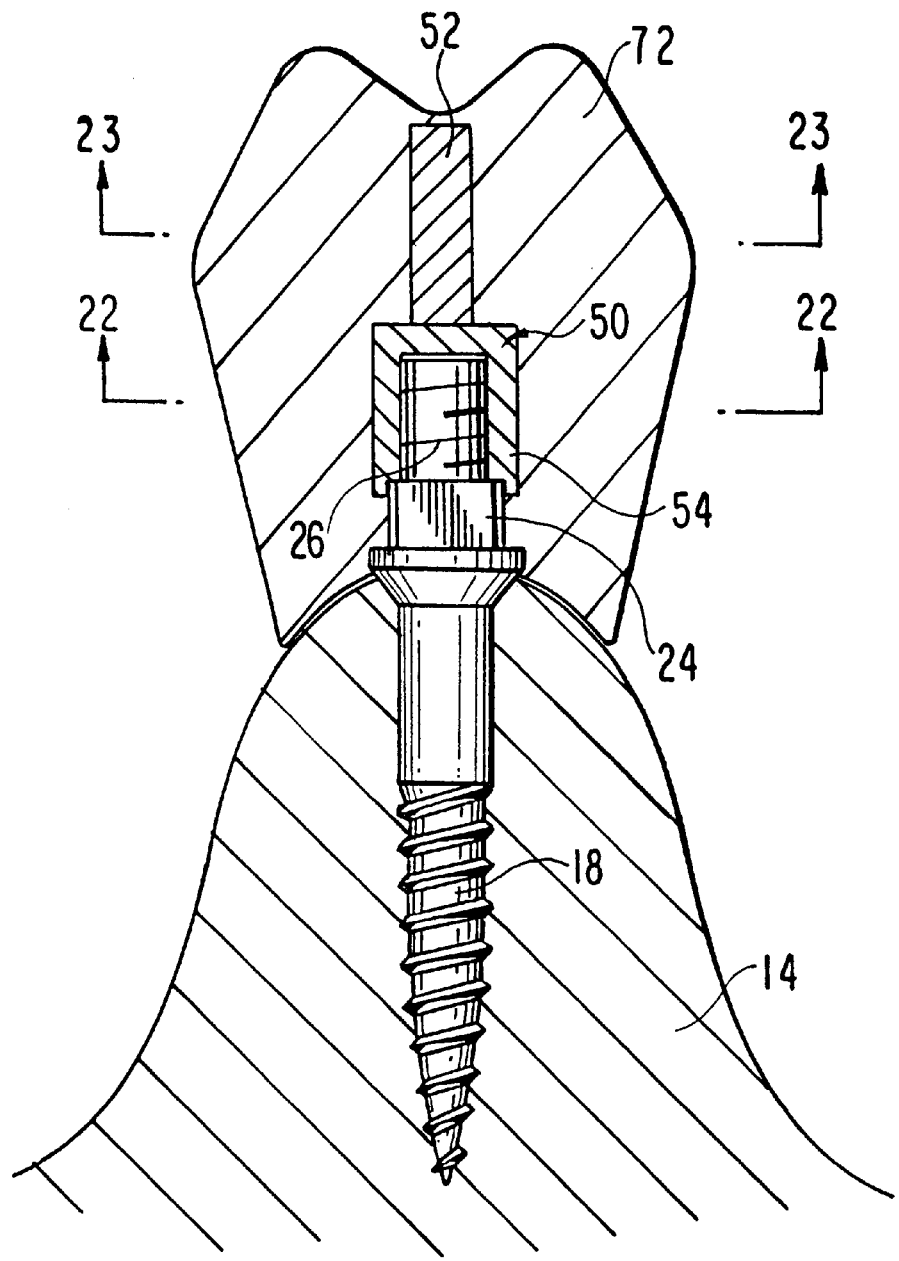
FIG. 21 illustrates a side cross-sectional view of the artificial tooth mounted on an implant screw.

The implant screws of this invention can be used for supporting a single tooth prosthesis, as shown in FIG. 21, or can be combined in a modular system to form the foundation, or splint, for a full or partial denture prosthesis, as shown generally in FIG. 20.

Figure 6:
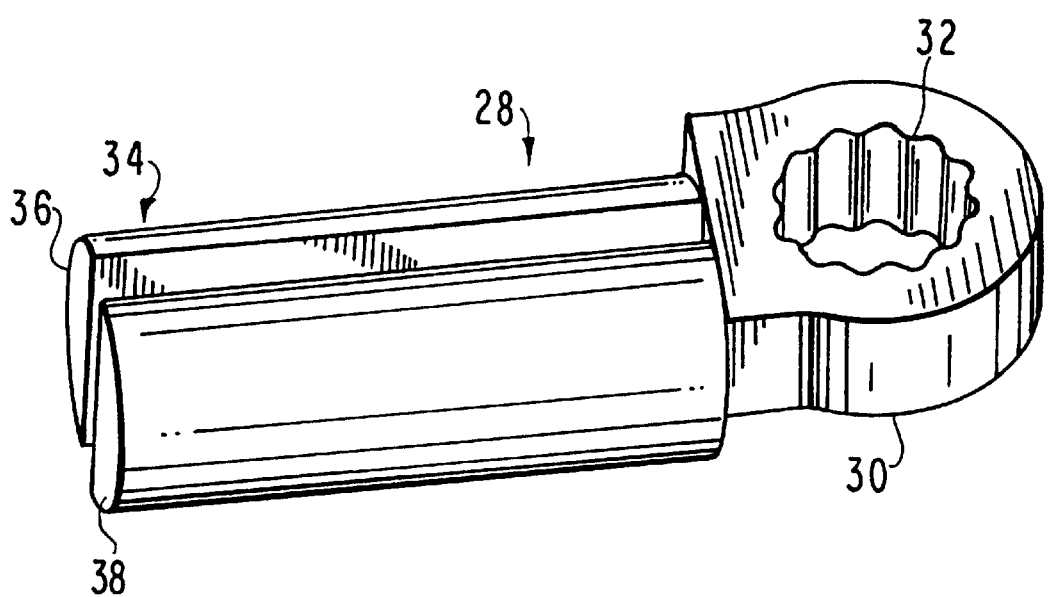
FIG. 6 illustrates a perspective view of a engineer's drawing of a side-extending implant platform.
Figure 7:
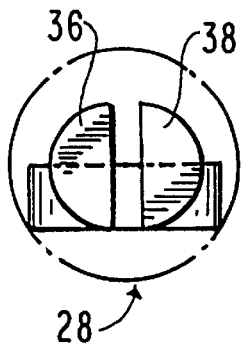
FIG. 7 illustrates a front plan view of the side-extending implant platform of FIG. 6.
Figure 8:
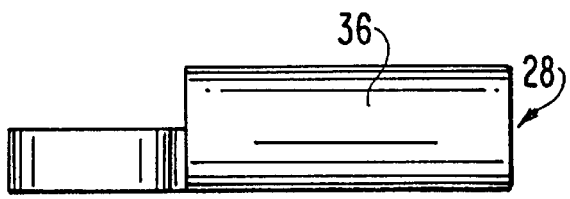
FIG. 8 illustrates a side plan view of the side-extending implant platform of FIG. 6.
Figure 9:
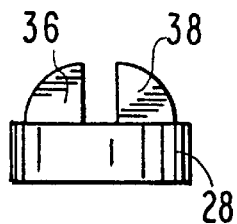
FIG. 9 illustrates a rear plan view of the side-extending implant platform of FIG. 6.
Figure 10:
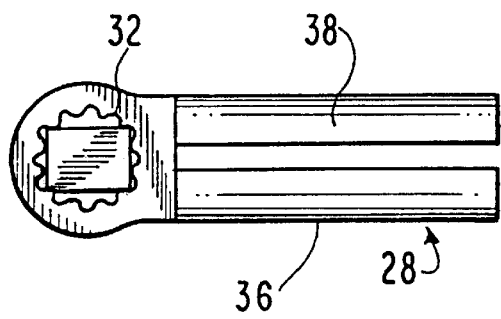
FIG. 10 illustrates a top plan view of the side-extending implant platform of FIG. 6.
Figure 11:
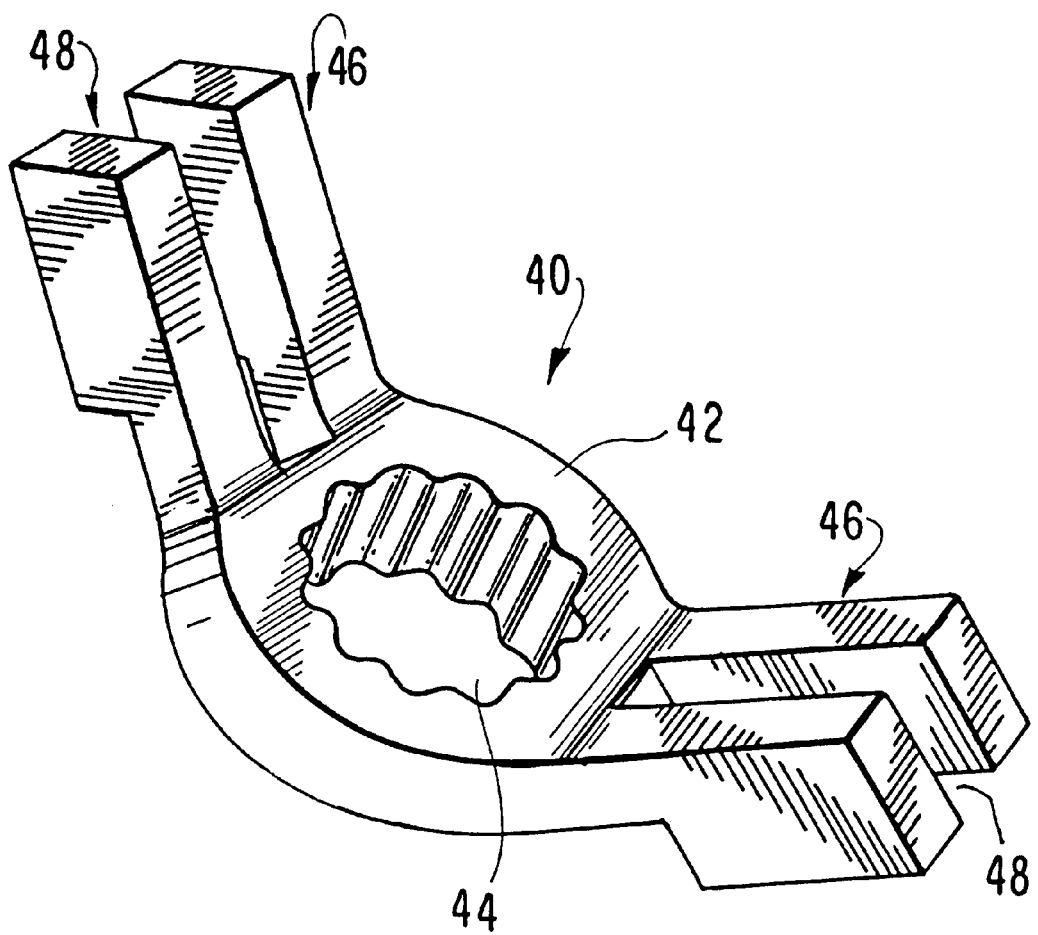
FIG. 11 illustrates a perspective view of a engineer's drawing of an angular implant platform.

When assembling the modular system, after the implant screws 18 are secured in place into the hard dental material, an indexing modular member, such as the double slot member 60, as shown in FIGS. 11–13, the single slot member of FIG. 6, or the multi-slot 80 (refer to FIGS. 55–61 and FIG. 73 shown in an exploded view) is mated to the driving portion 24 so as to orient the slots defined by the directional arms 62 or slot arms 82, which will hold a connecting bar member 84 in a desired linear direction, and if necessary, at a desired elevation axially relative to the implant screws. The internal circumference of the indexing member 80 mates with the driving portion of the implant screw so as to maintain the desired angular position with respect the jawbone ridge, as shown in FIG. 19.

Figure 73:
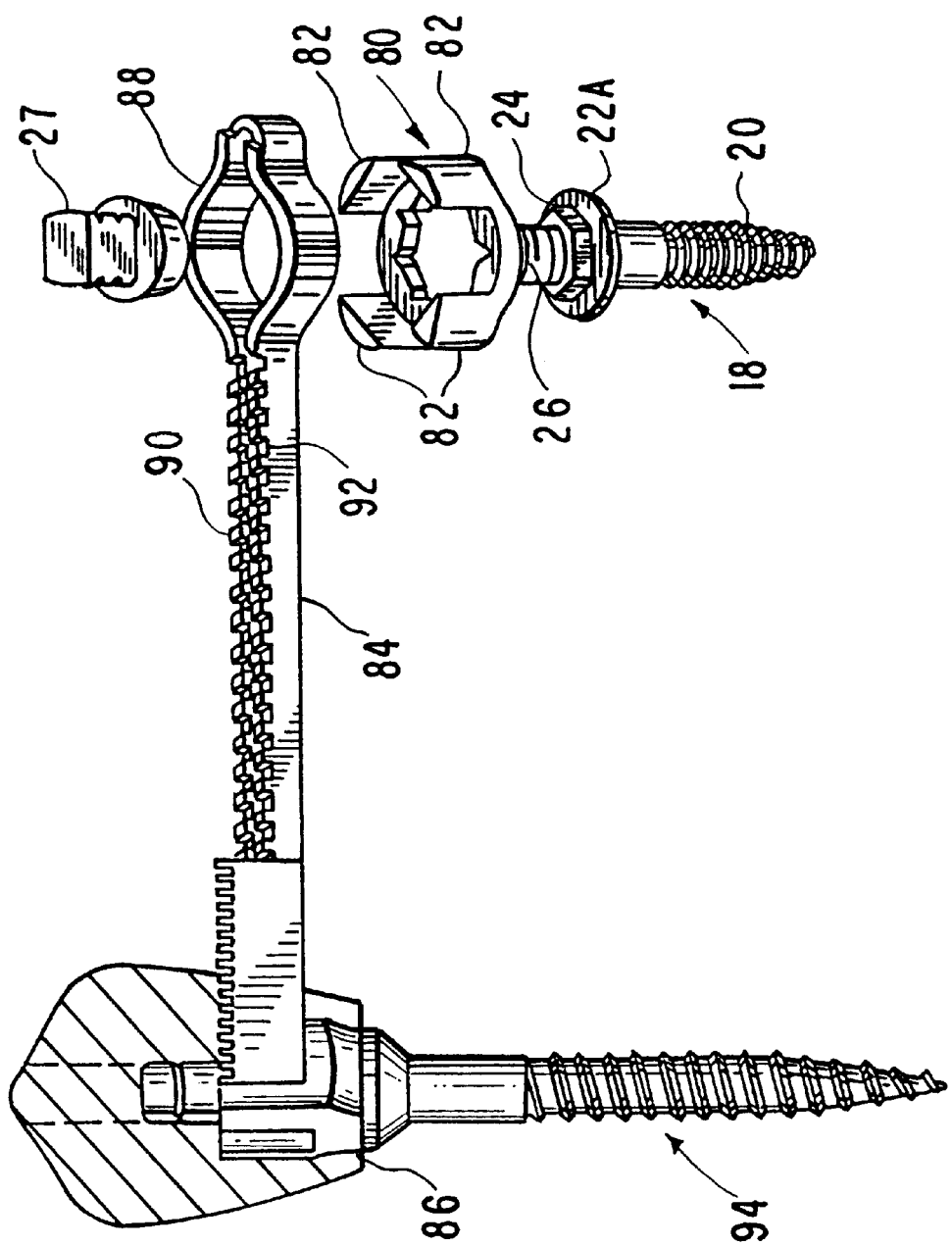
FIG. 73 illustrates an exploded perspective view of the combination of FIG. 72 at a first end of the end bar, with a second assemblage of screw, cap, and implant platform at a second end of the end bar.

A connecting bar member 84 extends between adjacent multi-slot indexing members 80, 86, as shown in FIG. 73. In the embodiment of FIG. 73, one of the implant screws shown is at one end of a foundation or splint. That end of the bar member 84 is folded on itself to form a closed loop 88 that surrounds the driving portion 24 of the end implant, and the folded pair of bars 90, 92 extends from that end support 88 to the next adjacent implant screw. In this case, the ends of the bars 90, 92 are each bent around an arm of the indexing member 80 so as to be locked in place to that second support member. If there are additional implant screws to be interconnected in this splint, the bars 90, 92 may be sufficiently long to pass through the slots between the arms 62, of the immediately adjacent indexing member, e.g., as shown in FIG. 19A, and extending onto a third implanted support.

Alternatively, as in the embodiment comprising a total of only two implant support screws, as shown in FIG. 73, a second pair of bars are wrapped around and extend from two other indexing arms 82, on the indexing member 80, on the second implant support 18, to a third implanted support, and so on. At the second end of the series of support posts forming the longer splint, the final bar member can be a substantial mirror image of the first member, having a looped portion surrounding the driving portion 24 of the final support implant screw. It can be preferable to utilize a series of separate pairs of connecting bars 90, 92, especially where there are significant variations in the jawbone ridge, or in the teeth of a patient. By assembling the system in this manner, the variations in elevation or size of a jawbone ridge or teeth stub can be accommodated without irritation to the patient, thus permitting a dentist to easily provide a structural support for a patient that does not cause irritation and can be easily constructed.

Preferably following the placement of the connecting bars 90, 92, on the indexing members of the prosthesis connecting member 26, the locking screw caps 27 can be screwed onto the connecting member 26 of each implant screw 18, so as to secure the indexing member 80 onto the support screw 18 without interfering with the movement of the connecting bars 90, 92. Preferably, the final locking cap 27 is placed after the connecting bars 90, 92 are in place, but before the connecting bars 90, 92 are bent around the index posts 82. In this manner, the indexing member 80 is firmly held onto the screw 18 before the connecting bars 90, 92 are locked in place.

Figure 16:
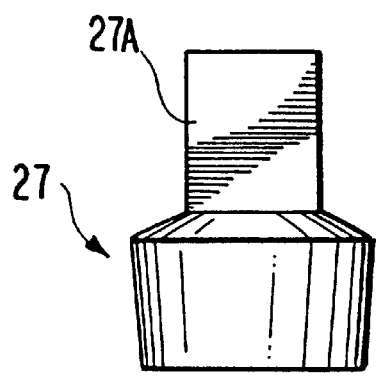
FIG. 16 illustrates a side plan view of the cap of FIG. 15.

The cap 27 is also provided with a longitudinal extension distal from the support screw 18 to enable assembly and/or subsequent removal of the cap 27 from the implant screw. The outer circumference of the cap 27 preferably has a taper, as shown in FIG. 16, tapering inwardly towards the support screw platform 22A. This permits easier removal after the acrylic cement and/or resin has been poured in place around the support screw system.

The longitudinal extension 27A of the cap 27, can be a shaft, as shown in FIGS. 32–35, or a slotted sphere, as is shown in FIGS. 88–91. The shaft 27a is originally longer than desired, for ease of assembly, but preferably can be cut or ground down after the cap 27 is in place, to a length depending upon the size of the ultimate prosthesis. However, a portion of the longitudinal extension 27A preferably remains in order to permit subsequent removal of the cap 27. The ultimate length of the longitudinal extension 27A depends upon the distance to the opposing teeth and the desired size of the tooth prosthesis, in effect acting as a stop for the opposing teeth.

After the locking cap 27 is in place, the connecting bars 90, 92 are then secured to the indexing posts 82 by being looped around and doubled back along the connecting bar length, so as to hold the connecting bar member 84 between two adjacent support screws 18. After a succession of support screws 18 are interconnected, each by at least a pair of connecting bars 90, 92, the entire modular system is preferably encased in resin, preferably any of several known self-curing resins available to the dental practitioner, in order to lock the system into position with the connecting bars 90, 92, as shown in FIG. 20, acting in effect as reinforcement for the resin.

Figure 68:
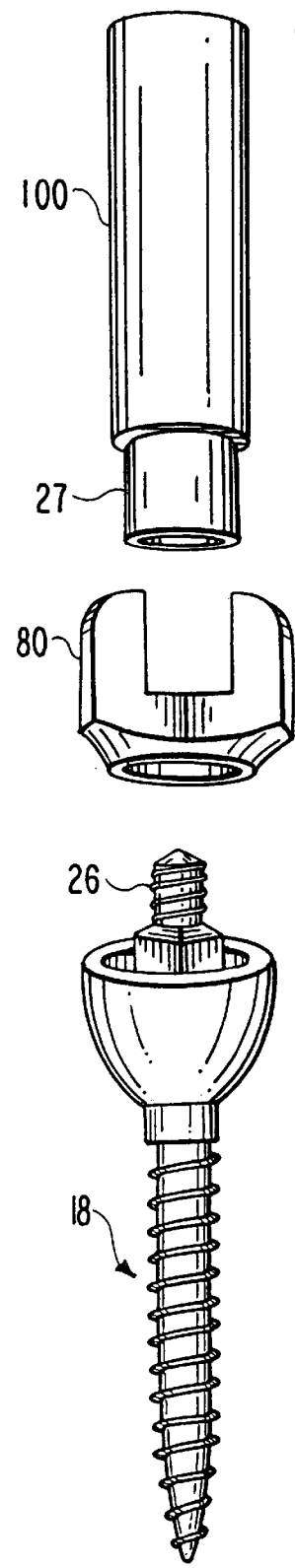
FIG. 68 illustrates an exploded side view of the assemble of FIGS. 63 and 67.

Preferably, prior to forming the resin around the modular system, a protective sleeve 100, such as shown in FIG. 26–27 and made of a material that does not adhere to the resin used, such as a silicone polymer, is placed around each of the caps 27, extending the full length of the extension 27a, as shown in the exploded view of FIG. 68, in order to permit removal of the cap after the resin has hardened. The silicone sleeve 100 extends substantially above the height of the longitudinal extension 27A, in order to ensure that the top of the extension 27A is not covered by any curing resin. This permits ready removal of the cap, thus unlocking the resin encased splint, or modular form, from the implant screws 18.

Figure 78:
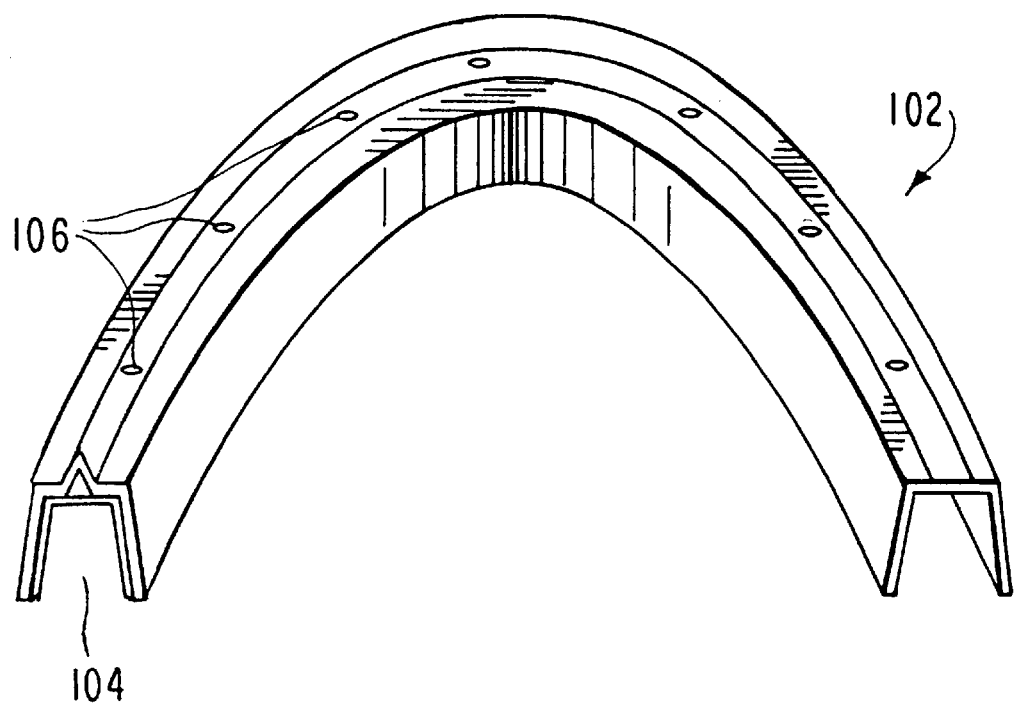
FIG. 78 illustrates a perspective view of a mold for use in forming resin into a solidified foundation about a split.

As shown in FIG. 78, a mold or channel form 102 is utilized to apply the e.g., curable resin around the constructed modular system, in the patient's mouth, in a manner well-known in dentistry. The mold has an arched form, shaped so as to follow the curvature of the jaw or mouth. The channel form 102 can be formed of a thin, flexible material such as vinyl sheeting and of a clear or, at least, translucent material which enables a viewing of the molded material after the form is in place, and if desired the use of light to cure the resin, if it is not self-curing. Curable resin 104 is placed into the form 102 shown in FIG. 78, and the form 102 is then placed over the completed modular assembly, such as the overall assembly shown in FIG. 73. This permits the formation of a unitary prosthesis support in the general dentist's office without special equipment or specialized personnel. The channel form 102 is provided with openings 106 at its apex to permit the escape of air, thus preventing the formation of air bubbles in the hardened resin and enabling the dentist with a minimum of final grinding to achieve the desired smooth and continuous resin surface.

A denture 62, such as shown in FIG. 20, can be independently molded in preparation for fitting on the modular support system previously prepared and can be made in a normal fashion such that the teeth 64 mounted on the denture 62 properly mate with the opposing teeth in the mouth, and the support for the teeth can be made so that it fits over the prosthesis foundation or splint 10. The prosthetic teeth support 66 should be slightly larger than the usual such denture, so as to provide a channel on the surface opposite the teeth 64, that can fit over the unitary prosthesis support 10. The base of the denture 62 is formed so as to fit over the assembled prosthesis foundation 10.

Mating access holes 70 for the longitudinal extensions 27A, 52 are prepared in or through the denture 62, and if necessary through the tooth forms on the denture, so that access is available to the connecting member caps 27, 50. In this manner, the denture 62 is maintained in place in the mouth, with respect to the opposing teeth. The access openings should be of sufficient cross-section to permit access to the caps 27,50, such that the caps can be e.g., unscrewed, from the implant screws, and thus permit ready removal of the denture 62 and splint, for subsequent repair or cleaning.

Figure 17:
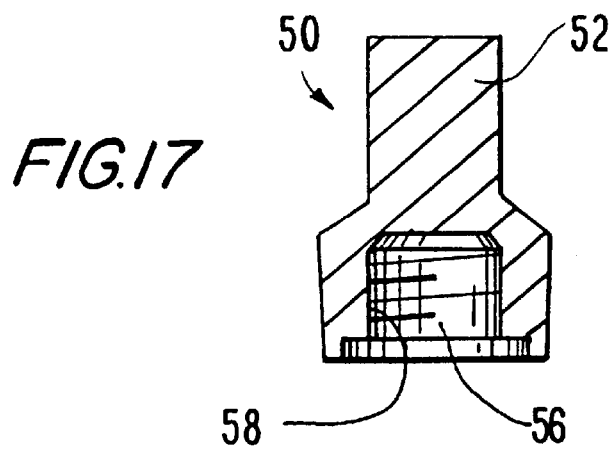
FIG. 17 illustrates a side cross-sectional view of the cap of FIG. 15.
Figure 18:
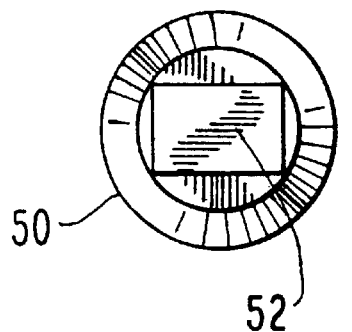
FIG. 18 illustrates a top plan view of the cap of FIG. 15.

When forming the denture, the position of the support screws 18 and the longitudinal extensions 27A of the caps 27, shown in FIG. 16, or alternatively the extensions 52 of the caps 50 shown in FIGS. 17 and 20, can be accommodated by marking the inner surface 66 of the denture 62 with the positions of the screws 18 and associated extensions 52. Holes 70 are drilled through the denture 62 which are sufficiently larger than the diameter of the longitudinal extensions 27A, 52 to permit a tool to be used to permit removal of the cap 27, 50 by accessing the respective longitudinal extensions 27A, 52 when necessary. The hollow bottom of the denture 62 is filled with an uncured resin 68 and the denture seated over the splint 10 such that the longitudinal extensions 27A, 52 extend into the prepared large holes 70, and the resin 68 cured such that the denture 62 is secured to the splint 10. The silicone sleeves 100, as described with reference to FIG. 29, covering the longitudinal extensions 27A, 52 extend through the openings 70 in the denture 62, thus maintaining the longitudinal extensions 27A, 52 free from being covered by the securing resin 68. After the resin 68 is set, the sleeves 100 may be removed and the openings covered by a soft material that would permit ready access to the longitudinal extensions 27A, 52. The denture 62 and the splint 10 can be secured together, such as by a cement or adhesive, so that the entire combined structure can be removed as a unit, leaving only the implanted screws 18. Alternatively the denture 62 can be made so as to be separable from the splint 10 by utilizing a "soft lining" 68 well known to those skilled in the dental profession which would frictionally hold the denture 62 in place on the splint 10 but be removable when desired to clean or change the denture 62. In this way the denture 62 is removable from the splint 10 and in turn, the splint 10 can be removable from the supporting implant screws 18 so each of them can be independently and separately cleaned or repaired.

FIGS. 3–5 illustrate side views of the implant screw 18 of FIG. 2 having variations in size and shape, such that longer screws may be secured, for example, into the sub-molar portions of the bone such as the jawbone 14, and shorter implant screws may be used for implanting into tooth stubs.

FIGS. 6–10 illustrate an alternative to the indexing members described above, which can be used for the end implant of a splint, as it has only a single slot opening. The mounting portion or base 30 has an indexing aperture 32 to engage the driving portion 24 of the screw 18, and can be indexed in a wide range of discontinuous angles in order to accommodate the direction of the bone ridge. The slot formed by the arms 36, 38 engages the connecting bars of e.g., member 84, shown in FIG. 32.

FIG. 11 illustrates a modular extension unit 40, having two slots for guiding the connecting bars, as shown, e.g., in FIG. 19. FIG. 19 illustrates the extension unit 40 as held in place by the cap 50 mounted on an implant screw 18 and securing a bridge component 12.

Figure 15:
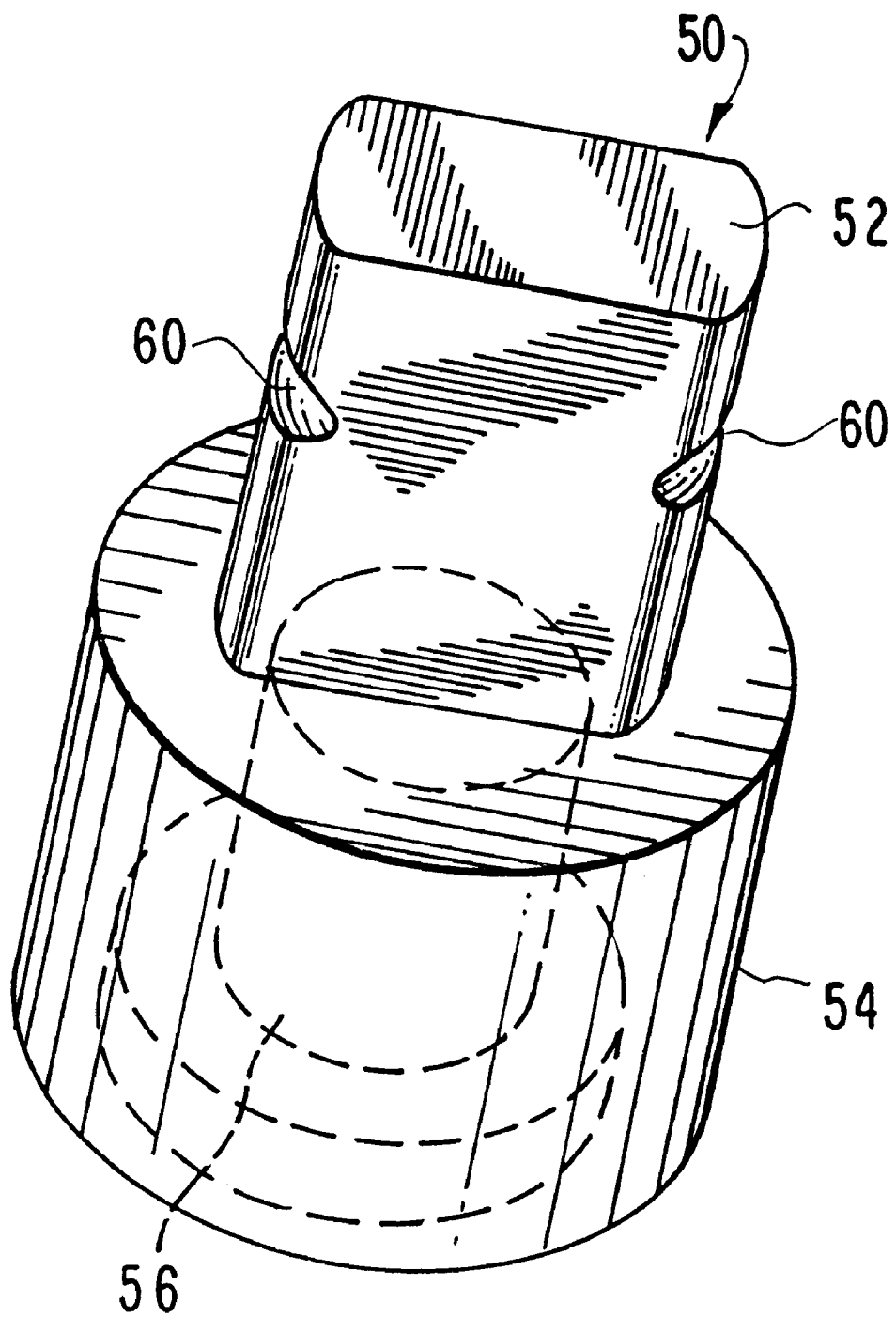
FIG. 15 illustrates a perspective view of a engineer's drawing of a cap for securing the implant platforms of FIGS. 6–14 to the implant screws of FIGS. 2–5.

FIG. 15 illustrates a perspective view of a engineer's drawing of a cap 50 for securing the implant platforms of FIGS. 6–14 to the implant screws of FIGS. 2–5, and FIGS. 16–18 illustrate various views of the cap 50 of FIG. 15. A rectangular extension 52 is positioned on a base 54 having a cavity 56 with an inner thread 58, shown in FIG. 17. The extension 52 is adapted to engage a compatible tool to cause the thread 58 to be screwed onto or from the prosthesis connecting member 26 of the screw 18. It is understood that the extension 52 need not be rectangular, but could be hexagonal, star-shaped, etc. Once positioned, the cap 50 is adapted to have the extension 52 engage corresponding apertures 70 in a denture 62, as described herein. In an example embodiment, shown in FIG. 16, the base 54 of the cap 50 is tapered.

FIG. 20 illustrates a prosthesis splint 10, mounted on the jawbone 14 by the modular components 28, 40 with caps 50 thereon, having the screws 18, and interconnected by bars/rails as the foundation 12. The interconnected components are fixedly secured in place by formation of the prosthetic bridge/splint 10 upon placement of self-curing resin, which may be acrylic, by using the mold 102 shown in FIG. 78. After a short time period, for example, 3–4 minutes, the self-curing resin hardens, thus forming the bridge/splint 10 over the foundation 12 with components 28, 40 mounted therein, as well as pins 58 which, typically, are mounted near the incisor and canine portions of the mouth. The pins 58 may be optional, and typically the screws 18 are positioned in the bicuspid and molar portions of the mouth on the bone 14.

As shown herein, the bone 14 is illustrated, for example, as the jawbone, but it is understood that the modular components disclosed herein are also capable of being mounted in the upper bones of the mouth, and not limited to use with only the jawbone.

Figure 34:
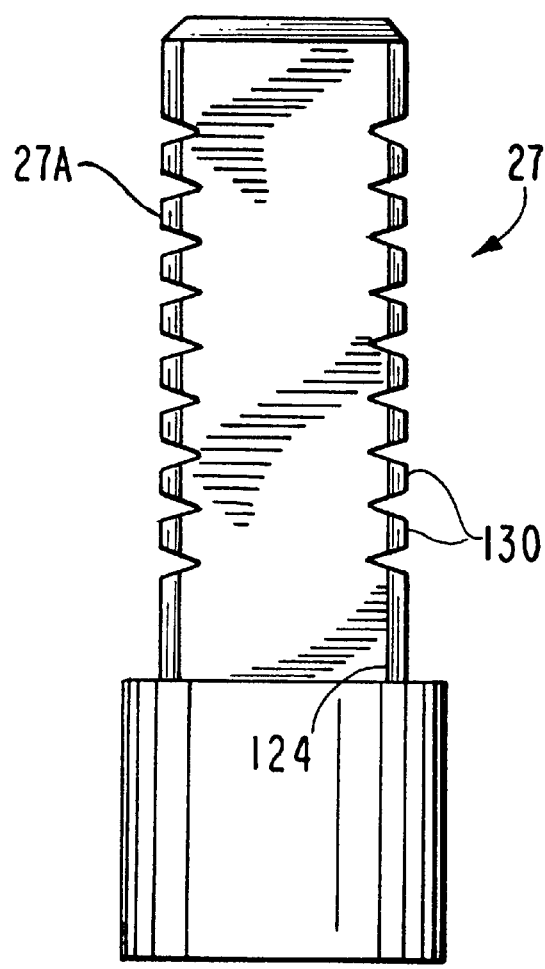
FIG. 34 illustrates a side plan view of the initial embodiment of a cap of FIGS. 15–18 prior to grinding down of the extension to a desired height.
Figure 35:
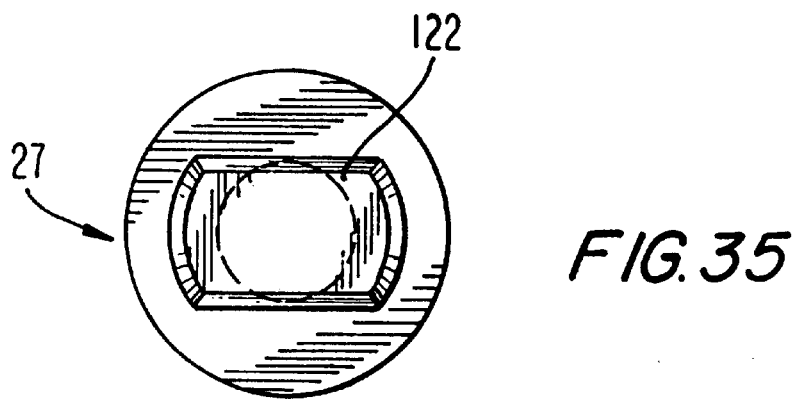
FIG. 35 illustrates a top plan view of the initial embodiment of a cap of FIGS. 15–18 prior to grinding down of the extension to a desired height.
Figure 42:
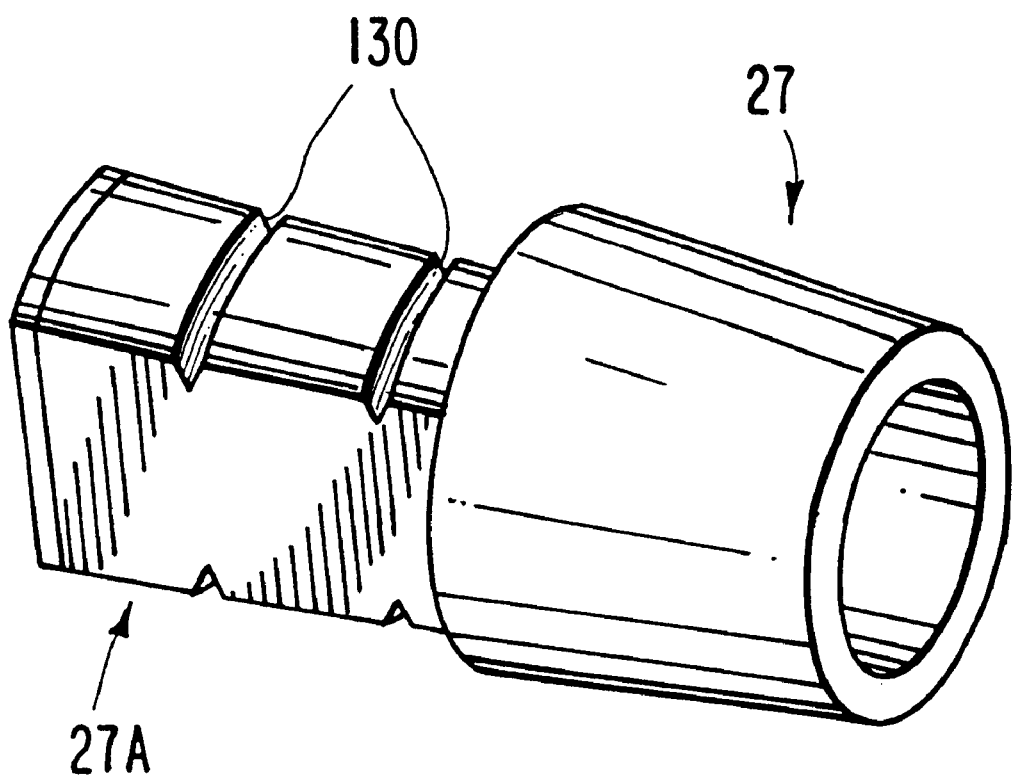
FIG. 42 illustrates a perspective view of the cap of FIGS. 32–35 after a grinding-down operation to a desired height.
Figure 43:
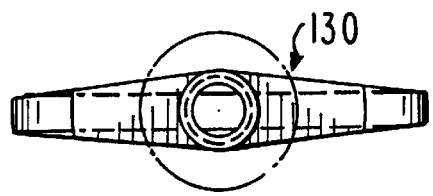
FIG. 43 illustrates a top plan view of an implant driver of FIG. 45.
Figure 44:
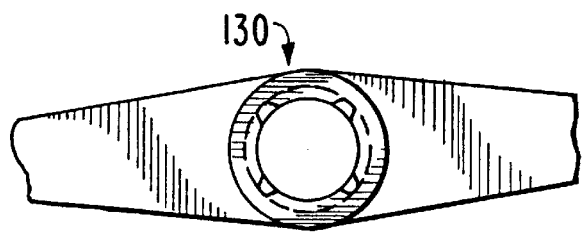
FIG. 44 illustrates a bottom plan view of the implant driver of FIG. 45, having a square aperture for engaging a square-shaped driving portion of the implant screw of FIG. 2.
Figure 45:
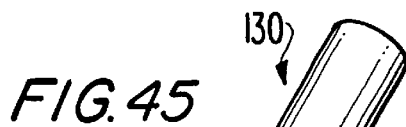
FIG. 45 illustrates a perspective view of the implant driver for driving an implant screw as in FIG. 2 into bone.
Figure 46:
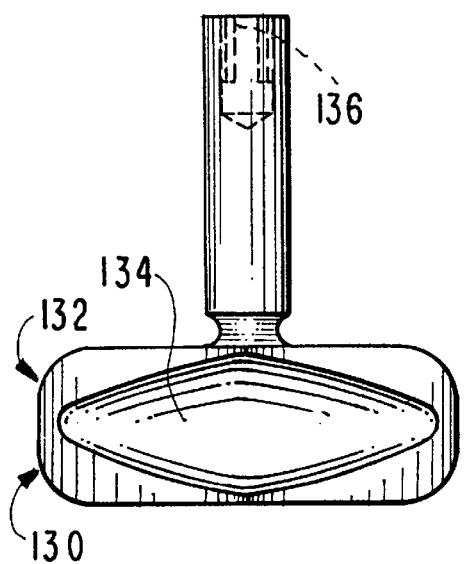
FIG. 46 illustrates a first side cross-sectional view of the implant driver of FIG. 45.
Figure 47:
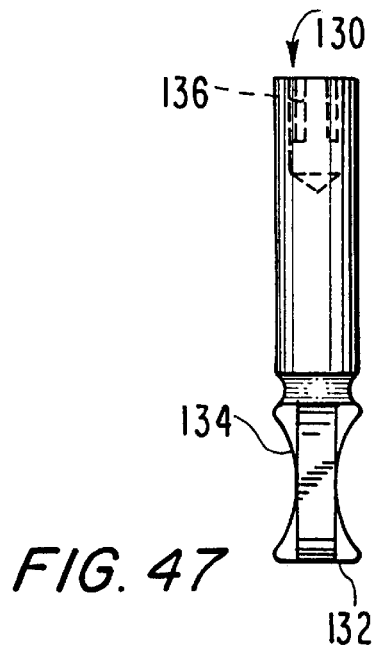
FIG. 47 illustrates a second side cross-sectional view perpendicular to the first side cross-sectional view of FIG. 46 of the implant driver of FIG. 45.

During formation of the acrylic bridge/splint 10, the caps 50 may be held firmly in place by drivers using a C-spring engaging a small groove 60 in the extension 52 of the cap 50 shown in FIG. 15, or grooves/indentations 130 shown in FIGS. 34 and 42. Once the acrylic bridge 10 is applied, for example, using vacuum techniques, and thence the acrylic hardens, the caps 50 may be, as needed, unscrewed from the components 28, 40. For example, at a later date, the bridge 10 may be removed and/or re-built to adjust the orientation of one or more components 28, 50 and/or the bars/rails and interconnected sections or splints of the foundation 12, for example, using conventional cutting tools and made to fit the ridge outline, height, and width.

As shown in FIG. 20, a denture 62 is adapted to engage the bridge 10 with caps 50 on components 28, 40. The denture 62 has tooth forms 64 and a continuous block base having an undercut cavity 66 in the underdenture, in which a soft relining material or resin 68 is disposed for mounting the denture 62 to the prosthesis bridge 10. The undercut cavity 66 also includes a plurality of openings 70 for engaging the caps 50 and, optionally, the pins 58.

The relining material 68 is used to cushion the impact of masticatory functions of opposing and firmly holding frictionally the teeth in place on the bridge 10. In another embodiment, notches 63 are formed in the acrylic bridge 10, to receive and mold with the relining material 68 for improved retention of the denture 62 to the bridge 10.

The soft relining material 68 may be any known resin or substance such as, for example, commercially available substances and/or other material such as "MUCUSOFT" available from "PARKEL".

Alternatively, C-type clamps may be formed upon or against the caps 50, for example, to utilize the taper of the base 54 of the caps, and then the C-type clamps are attached to the underside of the denture 62 to firmly hold the denture 52 in place for normal masticatory functions, yet the C-type clamps allow the denture 52 to be removably mounted to the bridge 10.

The underlying foundation 12, including the splint with modular components 28, 40, are held by the accessible caps 27, 50, with the extensions 27A, 52 allowing removal by compatible tools, and so providing access for periodic examination and maintenance. The firmly held splint has the components 28, 40 with a height of about 3.5–4 mm. to accommodate most limiting inner-jaw spacings. The components 28, 40 may be combined with implants shown, for example, in U.S. Pat. No. 5,575,651, which are held in place with cement. The combined functions eliminate the need for placing screw caps in the anterior area of the mouth where space is limited, thus preventing patient discomfort and loss of tongue space for normal voice effects and functions.

Figure 22:
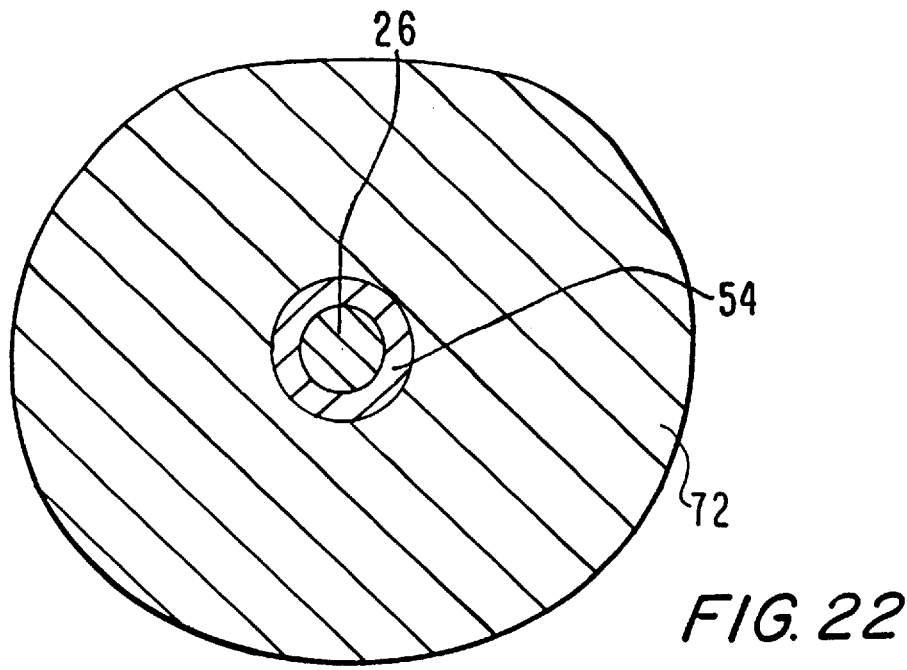
FIGS. 22 and 23 illustrate top cross-sectional views of the artificial tooth through lines 22—22 and 23—23, respectively.
Figure 23:
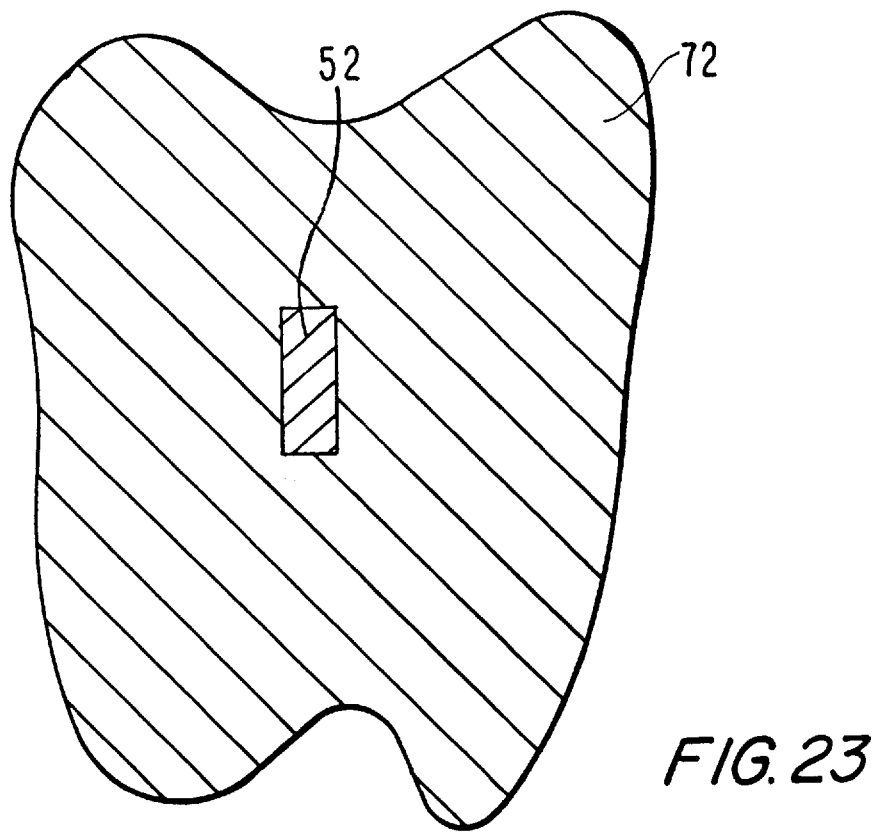

In another embodiment, FIG. 21 illustrates a side cross-sectional view of the artificial tooth 72 mounted on an implant screw, and FIGS. 22 and 23 illustrate top cross-sectional views of the artificial tooth 72 through lines 22—22 and 23—23, respectively. The artificial tooth 72 may be separate from the denture 62 shown in FIG. 20, and may be individually mounted upon the screw 18 extending from the ridge of the bone 14. In one embodiment, the artificial tooth 72 may include a hollow cavity for accommodating the screw 18 and cap 50. As shown in FIG. 21, it is understood that the dimensions and shape of the cap 50 may vary, for example, to include longer extensions 52 through entire height of the artificial tooth 72.

In another embodiment, the artificial tooth 72 may be integrally formed with the cap 50, such that the artificial tooth 72 includes threads in a cavity in the base 54 to be mounted onto the prosthesis connecting member 26 of the screw 18.

Variations may be made in the designs of the components and materials described herein. Sizes, shapes, and dimensions may be varied to accommodate different sizes and shapes of jaws, and also the disclosed invention and components may find diverse uses, for example, in the teeth of children and non-human animals. In addition, instead of slots, the components 28, 40 may be tubular to engage cylindrical rods as the bars of the foundation 12. The components may be composed of metal, as well as castable plastic or other substances. For example, the components may be formed using a lost wax process.

In addition, after an initial period of, for example, three months after the components 28, 40, the foundation 12, and the bridge 10 are applied, one may elect to make the configuration stronger. Depending on the composition of the components 28, 40, these components 28, 40 may be removed, for example, by unscrewing the caps 50, or alternatively by burning out the components, to be replaced by new components.

In addition, the components 28, 40 and other improvements described herein may be applied in conjunction with prior art dental prostheses, for example, by combining the components 28, 40 with previous components such as the pins 58, and so to be implemented around the old system present in the patient's mouth.

FIGS. 26–27 illustrate various views of a cap sleeve 100, which may be composed of silicone or other materials, and which fits onto the top of a cap 27, as shown in FIG. 68, during engagement with the insertion tool, to provide a more secure temporary engagement of the cap 27 and the insertion tool and to avoid stripping the edges of the cap 27 during rotation by the insertion tool during insertion or removal operations. The cap sleeve 100 may then be removed after the insertion tool disengages the cap 27 after insertion or removal operations.

Figure 28:
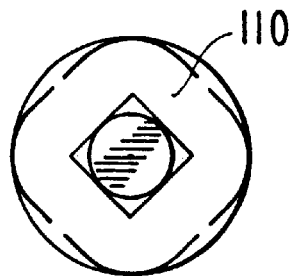
FIG. 28 illustrates top plan view of a cap insert tool disposed internal to the silicone cap sleeve of FIGS. 26–27.
Figure 29:
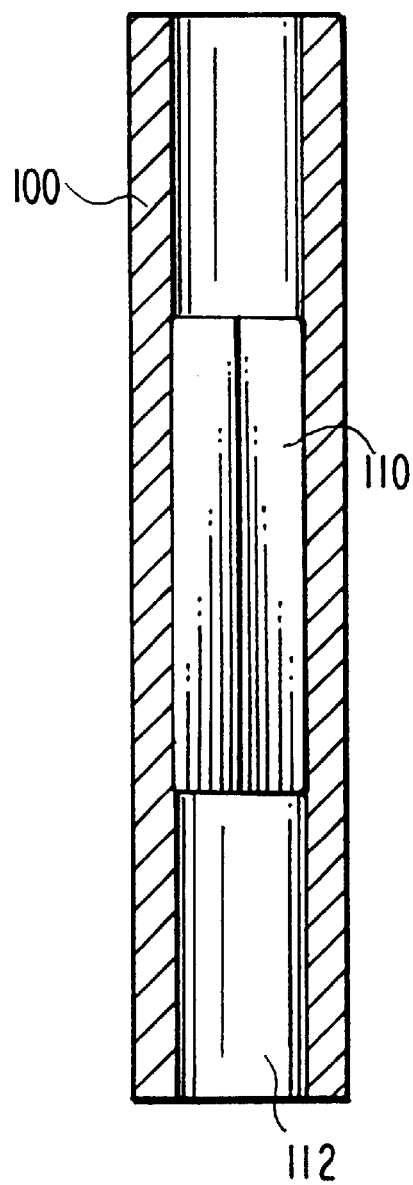
FIG. 29 illustrates a side cross-sectional view of a cap insert tool disposed internal to the silicone cap sleeve of FIGS. 26–27.

FIGS. 28–29 illustrate various views of a cap insert tool 110, with the silicone sleeve 100 surrounding the tool 110, with a space 112 provided to allow the tool 110 to engage the longitudinal extensions 27A of a cap 27.

Figure 30:
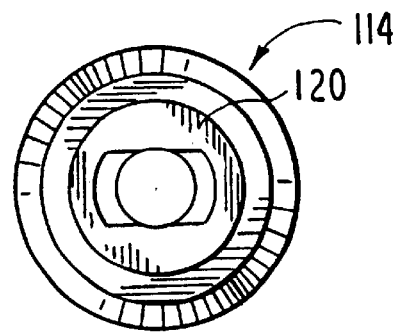
FIG. 30 illustrates a bottom plan view of a knurled cap driver, having a rectangular aperture for receiving and engaging the rectangular extension of the cap of FIGS. 15–19.
Figure 31:
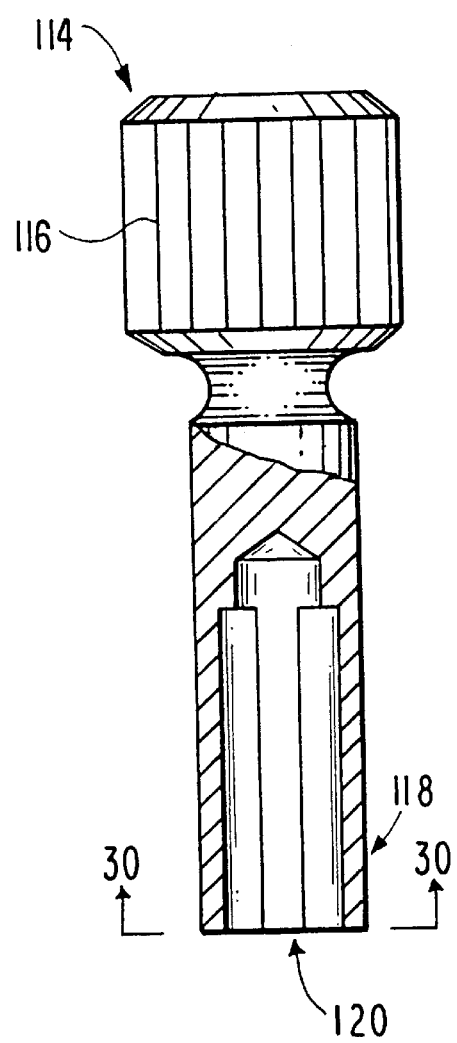
FIG. 31 illustrates a side cross-sectional view of a knurled cap driver, having a rectangular aperture at a lower end for receiving and engaging the rectangular extension of the cap of FIGS. 15–18.
Figure 32:
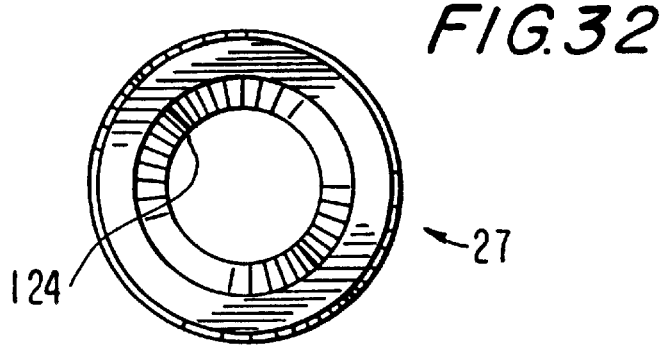
FIG. 32 illustrates a bottom plan view of an initial embodiment of a cap of FIGS. 15–18 prior to grinding down of the extension to a desired height.
Figure 33:
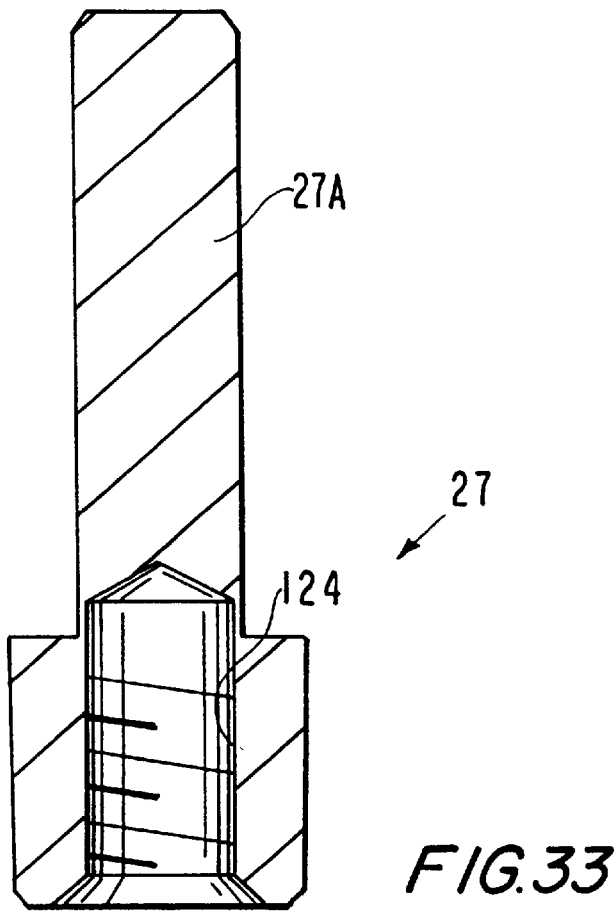
FIG. 33 illustrates a side cross-sectional view of the initial embodiment of a cap of FIGS. 15–18 prior to grinding down of the extension to a desired height.

FIGS. 30–31 illustrate various views of a knurled cap driver 114, with the knurled portion 116 providing gripping surfaces for manual turning to drive/insert a cap 27 engaged in the aperture 120 at a lower end 18 of the knurled cap driver 114. The aperture may be multi-faceted, such as a rectangular shape shown in the bottom view along lines 30—30, for removably engaging the rectangular extensions 27A, 52 of the cap 27, 50, as shown in FIGS. 15 and 19.

FIGS. 32–35 illustrate various views of alternative embodiments of an initial configuration of a cap 27. In particular, the embodiment of FIGS. 34–35 may include a rectangular cross-section 122, shown in FIG. 35, for engaging complementary rectangular-shaped apertures of the drivers, such as the driver 114 in FIGS. 30–32, and so to be driven by the driver to be secured to the prosthesis connecting member 26 of the screws 18, for example, to screw the threaded portion 124 of the cap 27 onto the threaded portion of the prosthesis connecting member 26.

Figure 36:
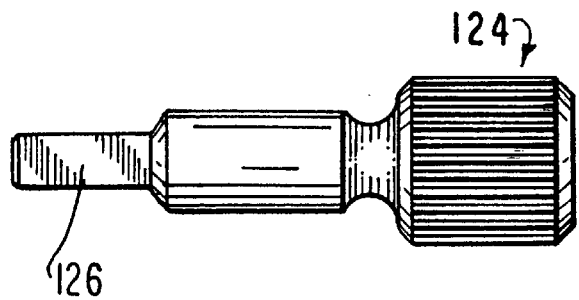
FIG. 36 illustrates a side plan view of a key for driving an implant screw of FIG. 2 into bone.
Figure 37:
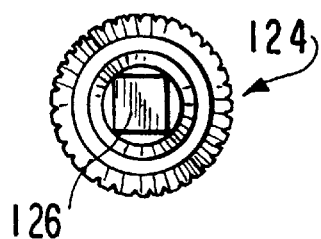
FIG. 37 illustrates a bottom plan view of the key of FIG. 36 having a square aperture for receiving a square-shaped driving portion of an implant screw for driving the implant screw of FIG. 2 into bone.
Figure 38:
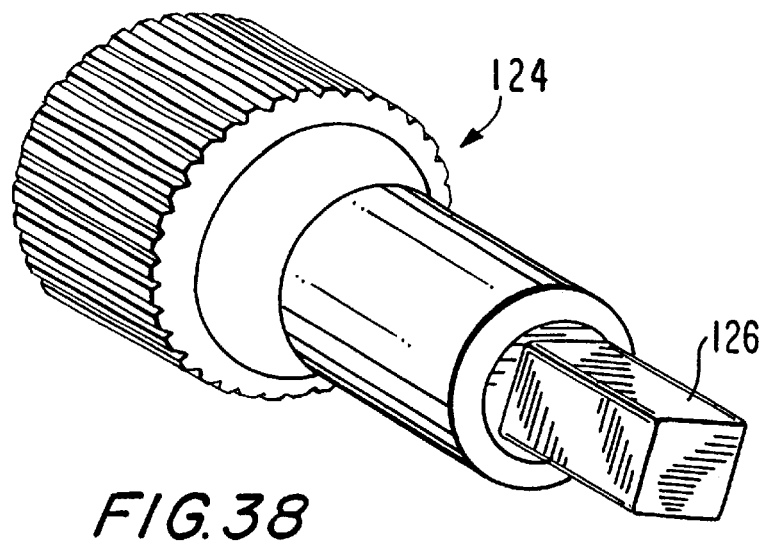
FIG. 38 illustrates a perspective view of the key of FIGS. 36–37 for driving an implant screw of FIG. 2 into bone.

FIGS. 36–38 illustrate various views of a key 124 having a knurled portion and a square aperture 126 for engaging complementary square-shaped driving portions 24 of the implant screws 18, allowing a dentist to manually screw the implant screws 18 into the jaw 14.

FIGS. 39–41 illustrate various views of an alternative embodiment of a cap key 128 with a square aperture 130 for engaging complementary shaped ends of a cap 27 for manual driving of the cap 27 onto the threaded prosthesis connecting member 26 of the implant screw 18.

FIG. 42 illustrates a perspective view of an alternative embodiment of the cap 27 of FIGS. 32–35 and 39–41, including indentations 130 into which the silicone sleeve 100 of FIG. 29 enters to provide a frictional fit, and so to remain positioned on the cap 27 during application of the resin or acrylic during formation of the splint 10. After the resin or acrylic has been formed and hardened, the silicone sleeve 100 may be removed from the cap 27. FIG. 42 also illustrates the reduction of length of the cap 27 from its initial configuration shown in FIGS. 32–35, to be a predetermined length determined by the dentist, with the cap 27 being grinded or otherwise portions being removed to a desired length, for example, to have the length of the cap 27 and its extensions 27A match the corresponding teeth opposite to the cap 27.

FIGS. 43–47 illustrate various views of an implant driver 130, having a gripping portion 132 with concave surfaces 134 for better manual gripping by fingers, and including a square aperture 136 at the distal end for removably engaging the driving portion 24 of the implant screw 18. Using the implant driver 130, a dentist may screw the implant 18 into the jaw 14, with the self-tapping threads 20 entering into and anchoring in the jaw 14.

Figure 48:
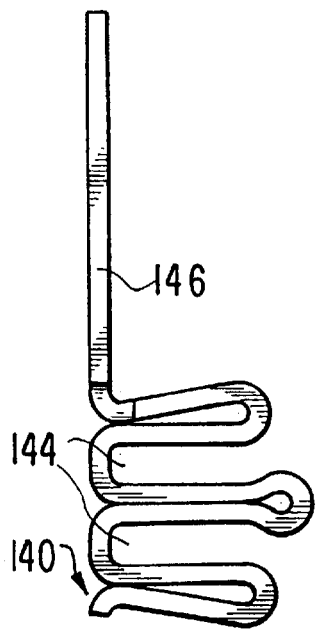
FIG. 48 illustrates a side plan view of an expander clip.
Figure 49:
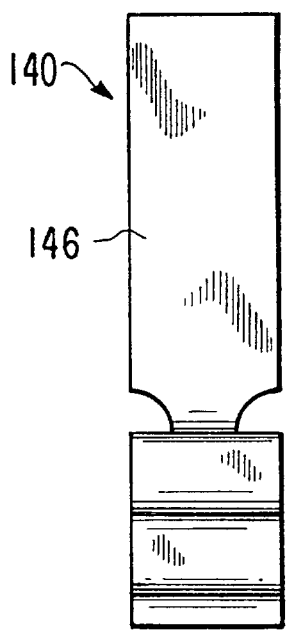
FIG. 49 illustrates a top plan view of the expander clip of FIG. 48.
Figure 50:
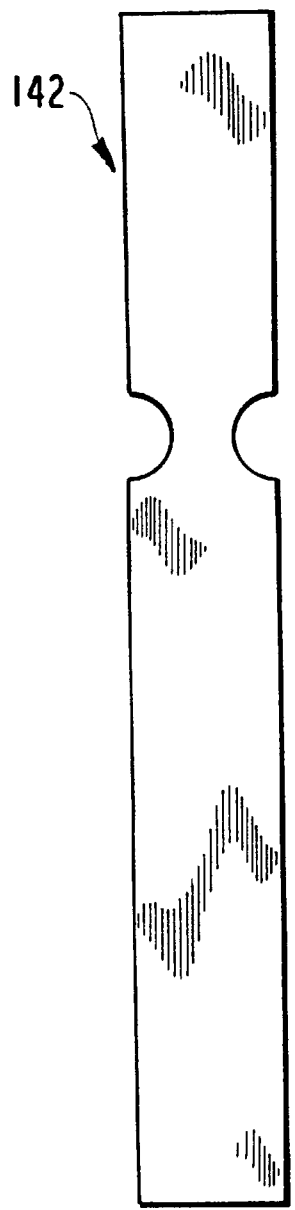
FIG. 50 illustrates a top plan view of a blank, as the initial configuration of the expander clip of FIGS. 48–49 prior to fabrication to the formed configuration of FIGS. 48–49.
Figure 55:
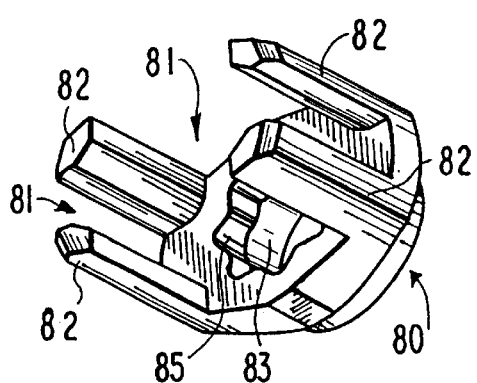
FIG. 55 illustrates a top perspective view of a four-slotted bucket-shaped implant platform.
Figure 56:
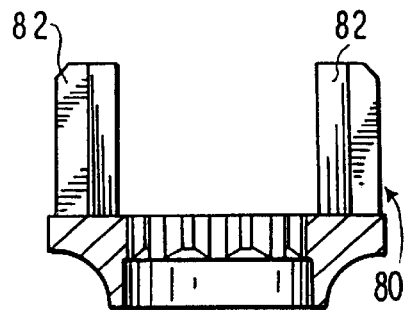
FIG. 56 illustrates a side cross-sectional view of the four-slotted bucket-shaped implant platform of FIG. 55.
Figure 57:
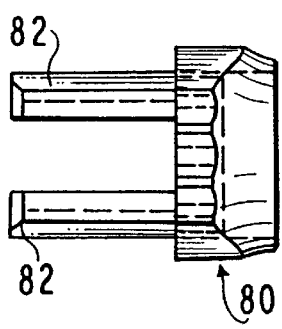
FIG. 57 illustrates a side plan view of the four-slotted bucket-shaped implant platform of FIG. 55, perpendicular in orientation to the side cross-sectional view of FIG. 56.
Figure 58:
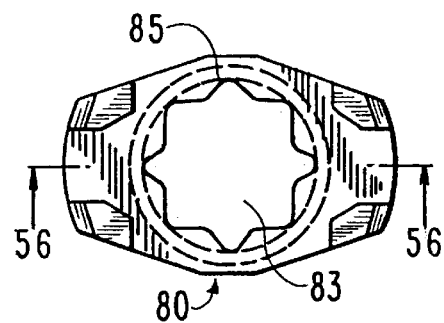
FIG. 58 illustrates a top plan view of the four-slotted bucket-shaped implant platform of FIG. 55.

FIGS. 48–50 illustrate various views of an expander clip 140, fabricated by folding an initially straight blank 142 of material, shown in FIG. 50, to form multiple slots 144 for engaging multiple bars, such as the bars 90, 92, forming the foundation, as shown in FIGS. 79–80, and with an extended portion 146 of the expander clip 140 extending from the slots 144. The extended 146 portion allows the dental technician to manipulate and position the expander clip 140 adjacent to the jaw 14 and in relation to the bars 90, 92 to be positioned therein, and then to break away the extended portion 146 after successful positioning of the expander clip 140 in the desired location. With the multiple bars 90, 92 expanded by the expander clip 140 to have a space therebetween, as shown in FIGS. 79–80, resin may enter the space and so, upon hardening of the resin, the formed foundation has added structural integrity. The expander clip 140 may similarly be fixedly positioned in the hardened resin and so, in conjunction with the bars 90, 92 in the resin, provide greater structural integrity to the formed foundation/splint.

FIGS. 51–54 illustrate various views of a spacer clip 150 having multiple slots 152 in a slotted portion 154 for engaging multiple bars 90, 92 forming the foundation, and with an extended portion 156 of the spacer clip 150 extending from the slotted portion 154. The extended portion 156 allows the dental technician to manipulate and position the spacer clip 150 to a desired position, and then to break away the extended portion 156 after successful positioning of the spacer clip 150. With the multiple bars 90, 92 expanded by the spacer clip 150 to have a space therebetween, as shown in FIGS. 81–82, resin may enter the space and so, upon hardening of the resin, the formed foundation has added structural integrity. The spacer clip 150 may similarly be fixedly positioned in the hardened resin and so, in conjunction with the bars 90, 92 in the resin, provide greater structural integrity to the formed foundation/splint.

Figure 59:
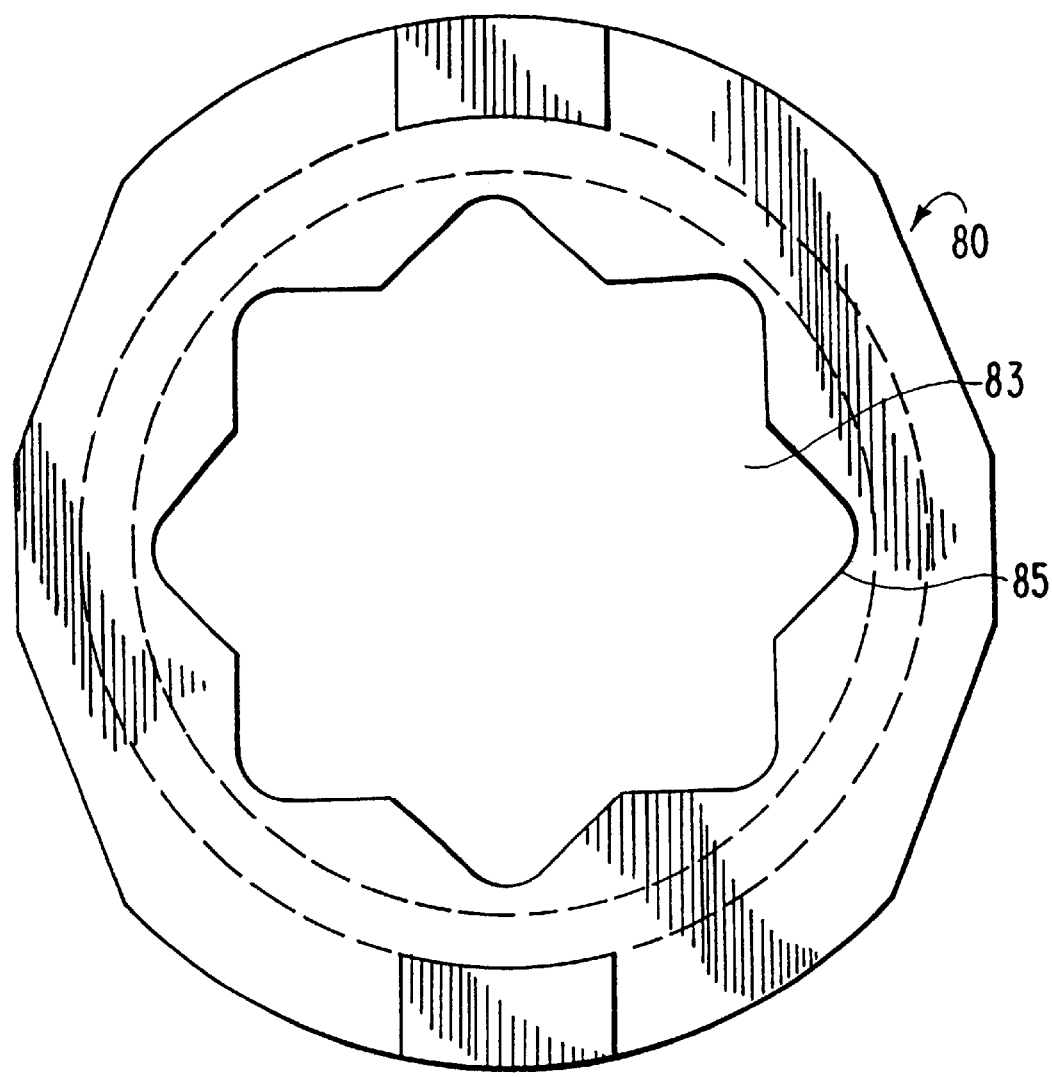
FIG. 59 illustrates a top plan view of a base of the four-slotted bucket-shaped implant platform of FIG. 55.
Figure 60:
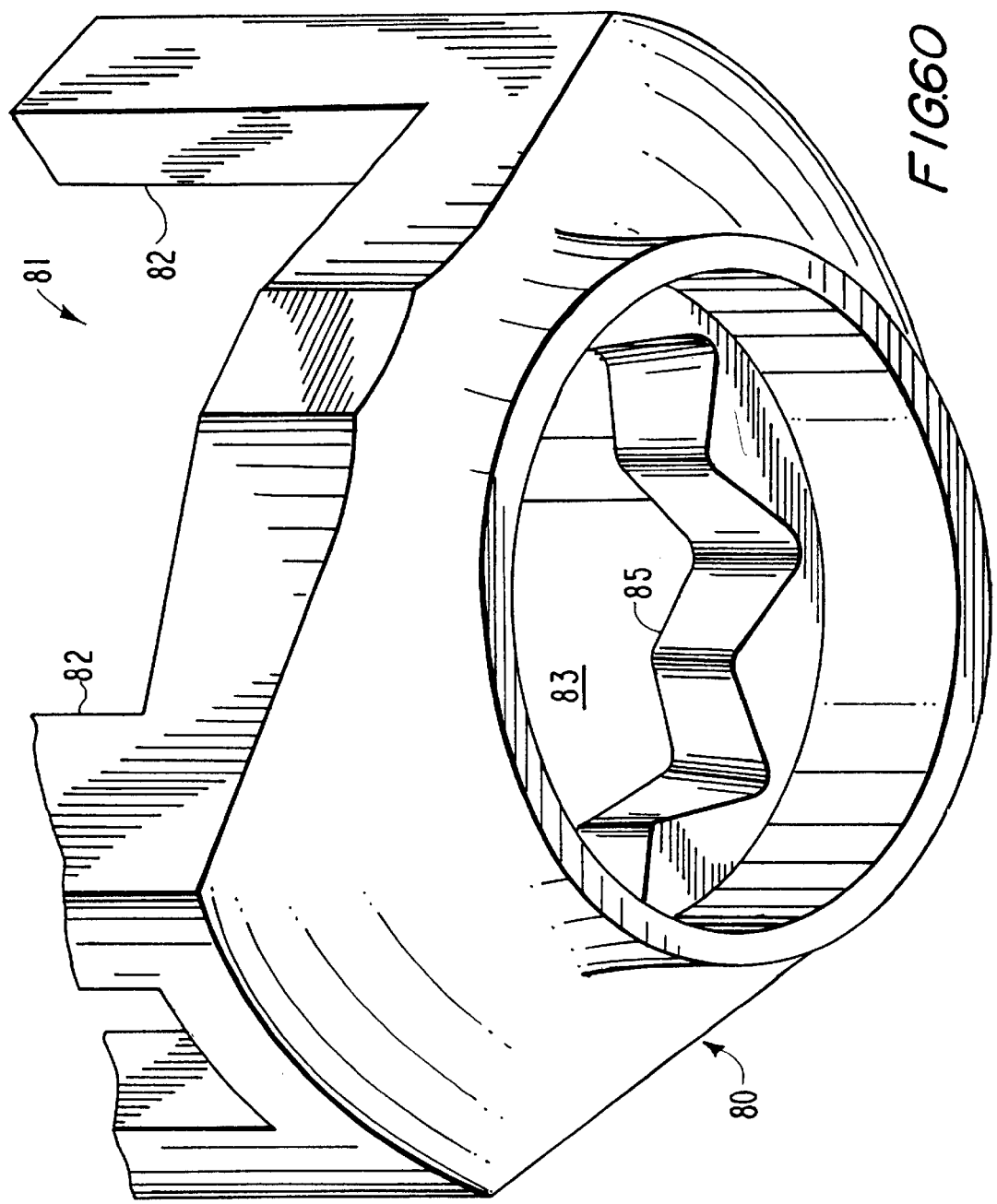
FIG. 60 illustrates a bottom perspective view of the four-slotted bucket-shaped implant platform of FIG. 55.
Figure 61:
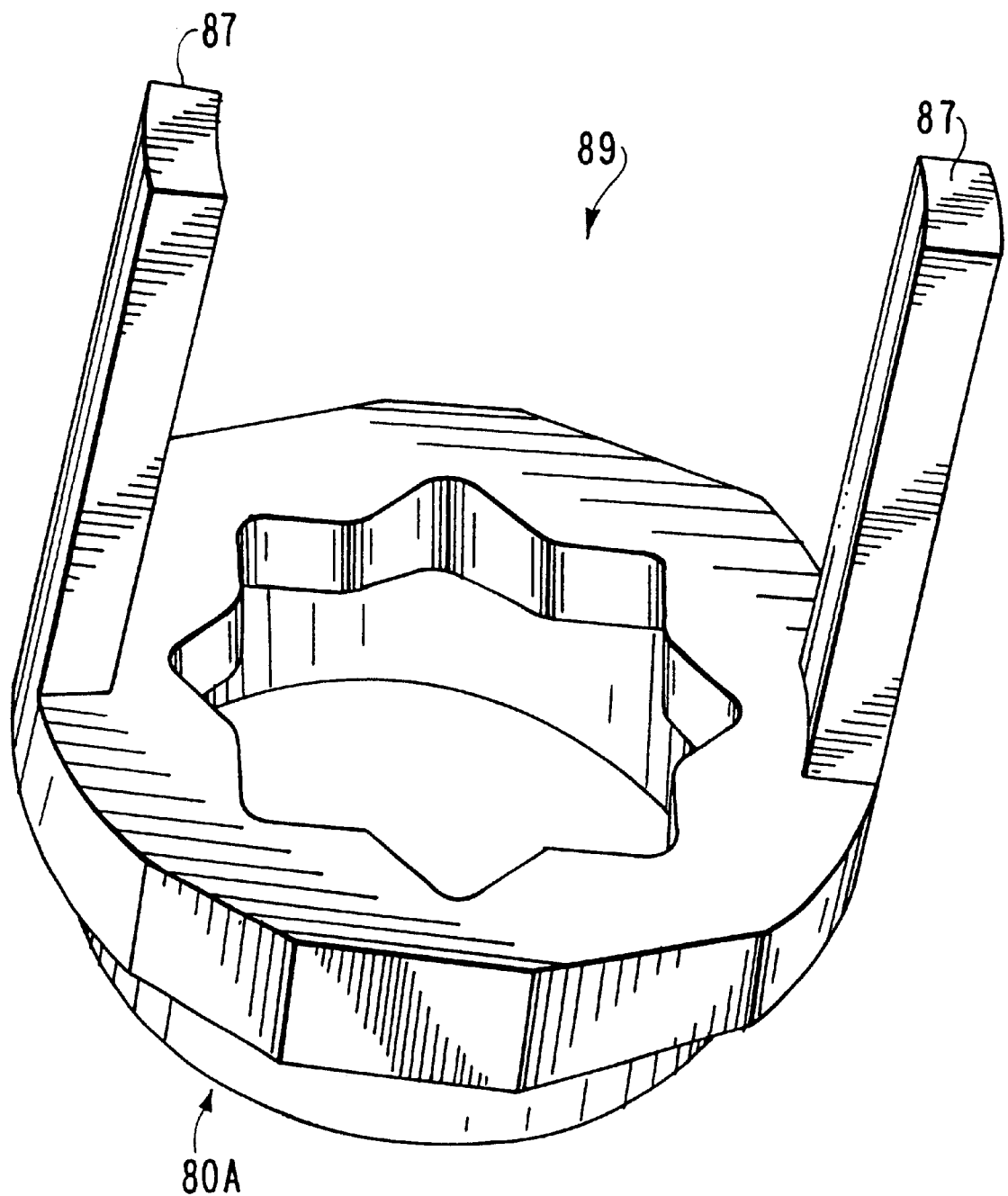
FIG. 61 illustrates a perspective view of a two-slotted embodiment of a bucket-shaped implant platform.

FIGS. 55–61 illustrate various views of a bucket-shaped indexing member 80, being an alternative embodiment of the angular indexing member 40 of FIGS. 11–14, providing multiple slots 81 formed by the posts 82 in different directions for positioning and orienting different bars 90, 92 forming the foundation, as shown in FIG. 73. In particular, FIG. 59 illustrates in greater detail the inner aperture 83 having multiple indentations 85 to provide a strong engagement with the multi-faceted driving portion 24 of a screw 18. In one embodiment of the indexing member 80, shown in FIGS. 55–60, four posts 82 form four slots 81, and in another embodiment, the indexing member 80A, shown in FIG. 61, has two posts 87 forming two slots 89.

Figure 62:
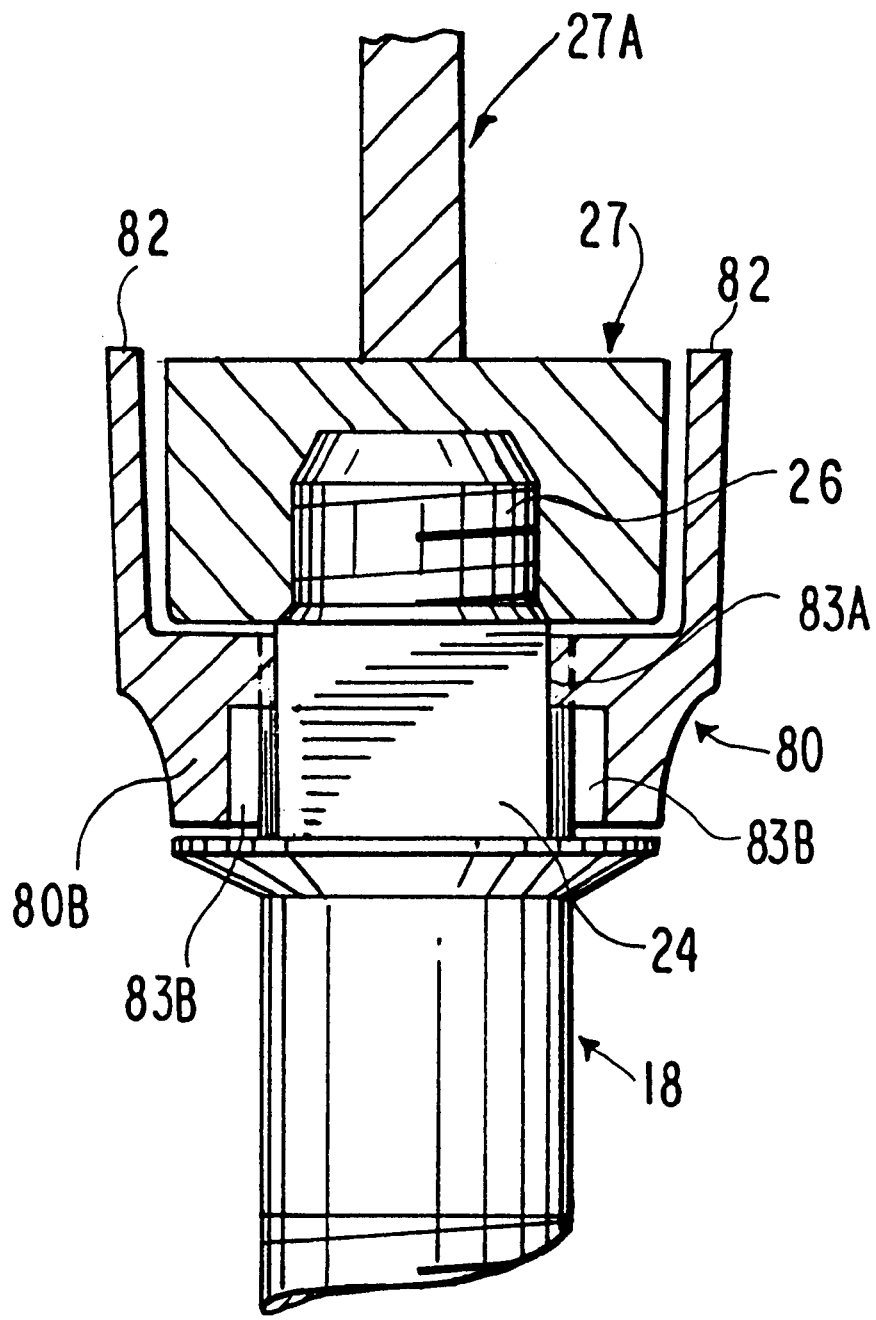
FIG. 62 illustrates a side cross-sectional view of the bucket-shaped implant platform of FIGS. 55–61 disposed on a screw as in FIG. 2, with the cap shown in FIGS. 15–18 thereupon, and with bars mounted between the cap and posts of the bucket-shaped implant platform.
Figure 66:
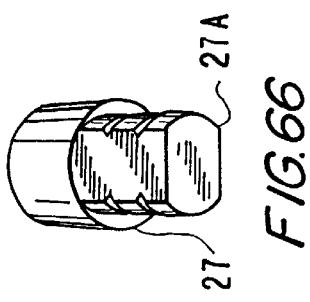
FIG. 66 illustrates a perspective view of the cap of FIG. 15 included in the assemblage of FIG. 63.
Figure 65:
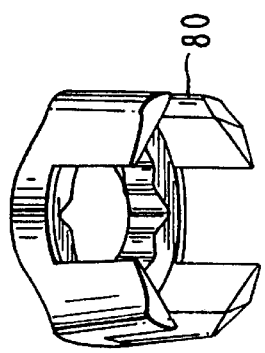
FIG. 65 illustrates a perspective view of the bucket-shaped implant of FIG. 55 and FIG. 63.
Figure 64:
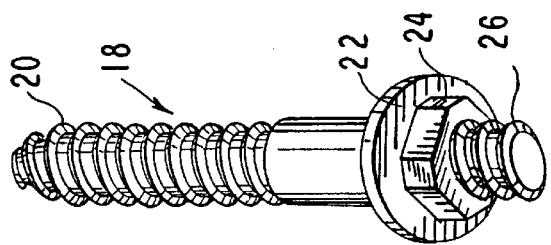
FIG. 64 illustrates a perspective view of the screw of FIG. 2 and FIG. 63.
Figure 63:
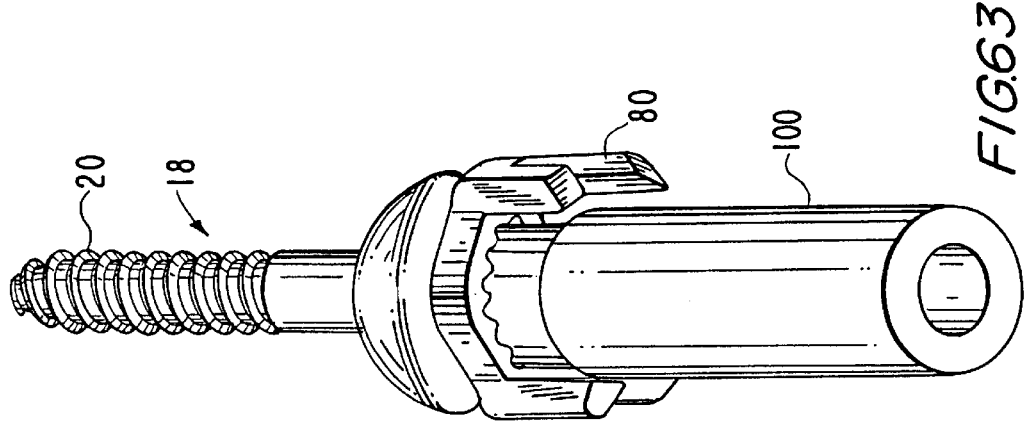
FIG. 63 illustrates a perspective view of an assemblage of the screw, the cap, and the bucket-shaped implant platform shown in FIG. 62, with the silicone sleeve of FIGS. 28–29 mounted to an extension of the cap.
Figure 67:
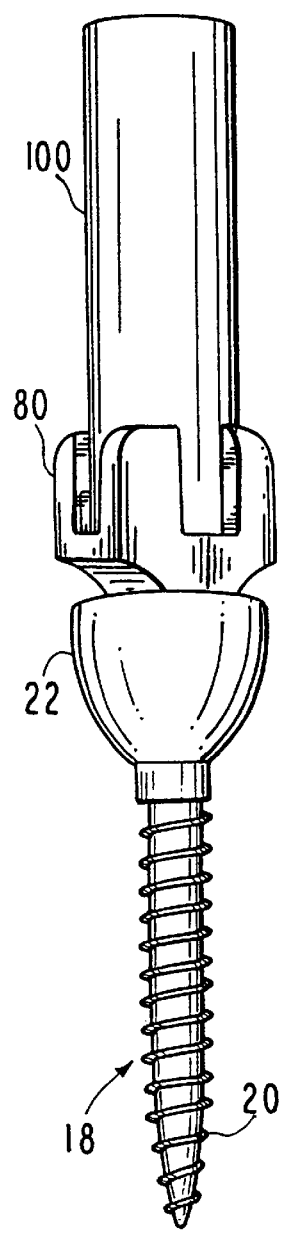
FIG. 67 illustrates a side plan view of the assemblage of FIG. 63.

FIG. 62 illustrates the bucket-shaped indexing member 80 of FIGS. 55–60 disposed on a screw 18, with the indentations 85 of the inner aperture 83 engaging the sides and edges of the multi-faceted driving portion 24 of a screw 18.

FIGS. 63–68 illustrate various views of the screw 18 and the bucket-shaped indexing member 80 in various stages of assembly with the cap 27 and sleeve 100.

Figure 69:
FIG. 69 illustrates a side plan view of an end bar.
Figure 70:
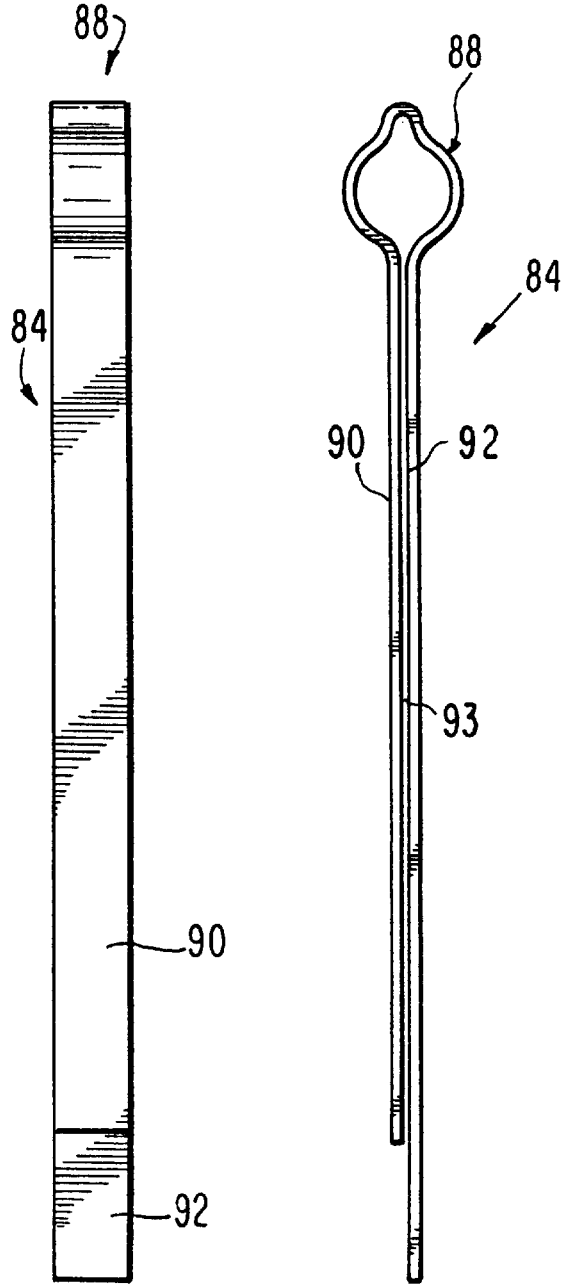
FIG. 70 illustrates a top plan view of the end bar of FIG. 69.
Figure 71:
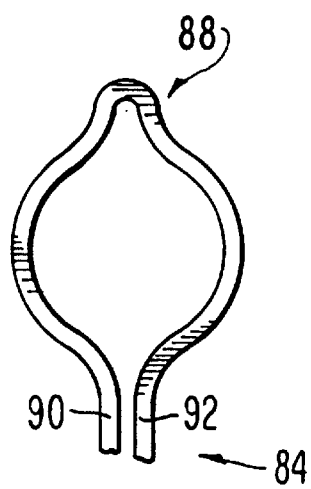
FIG. 71 illustrates a close-up top plan view of a loop at one end of the end bar of FIGS. 69–70.

FIGS. 69–71 illustrate various views of an end or connecting bar 84 having arms 90, 92 forming a loop 88 with a slot 93 therebetween for receiving the soft relining material, acrylic, and/or resin, and so providing superior structural integrity in forming the foundation in conjunction with the clips 140 and 150 in FIGS. 48–54, and described herein with reference to FIGS. 79–82. The connecting bar 84 has a loop 88 for fitting in the bucket-shaped implant member 80, and for fitting around the cap 27 on a screw 18, as shown in FIG. 73.

Figure 72:
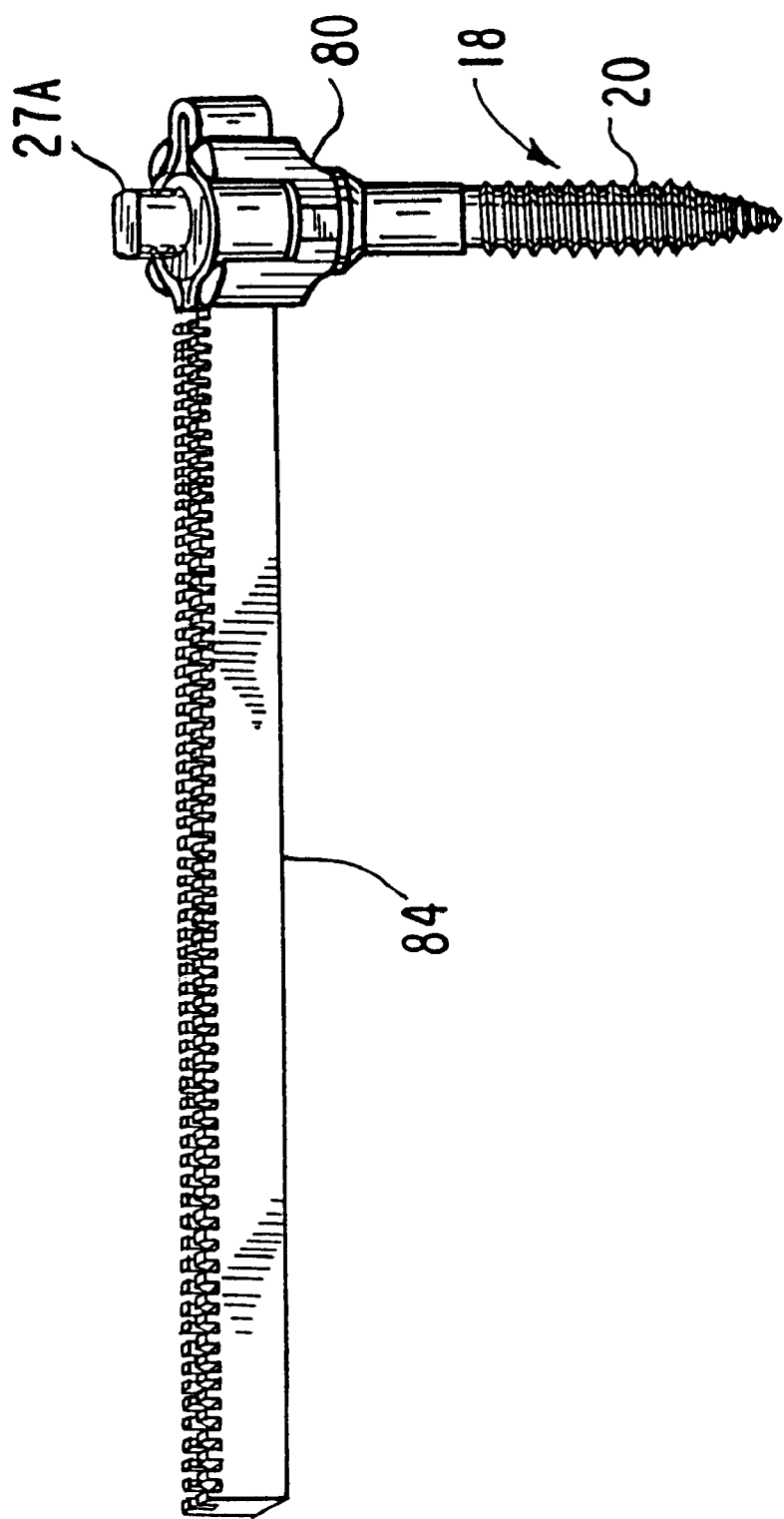
FIG. 72 illustrates a side plan view of the end bar of FIGS. 69–71 in combination with the assemblage of FIGS. 62–63 and 67–68.
Figure 74:
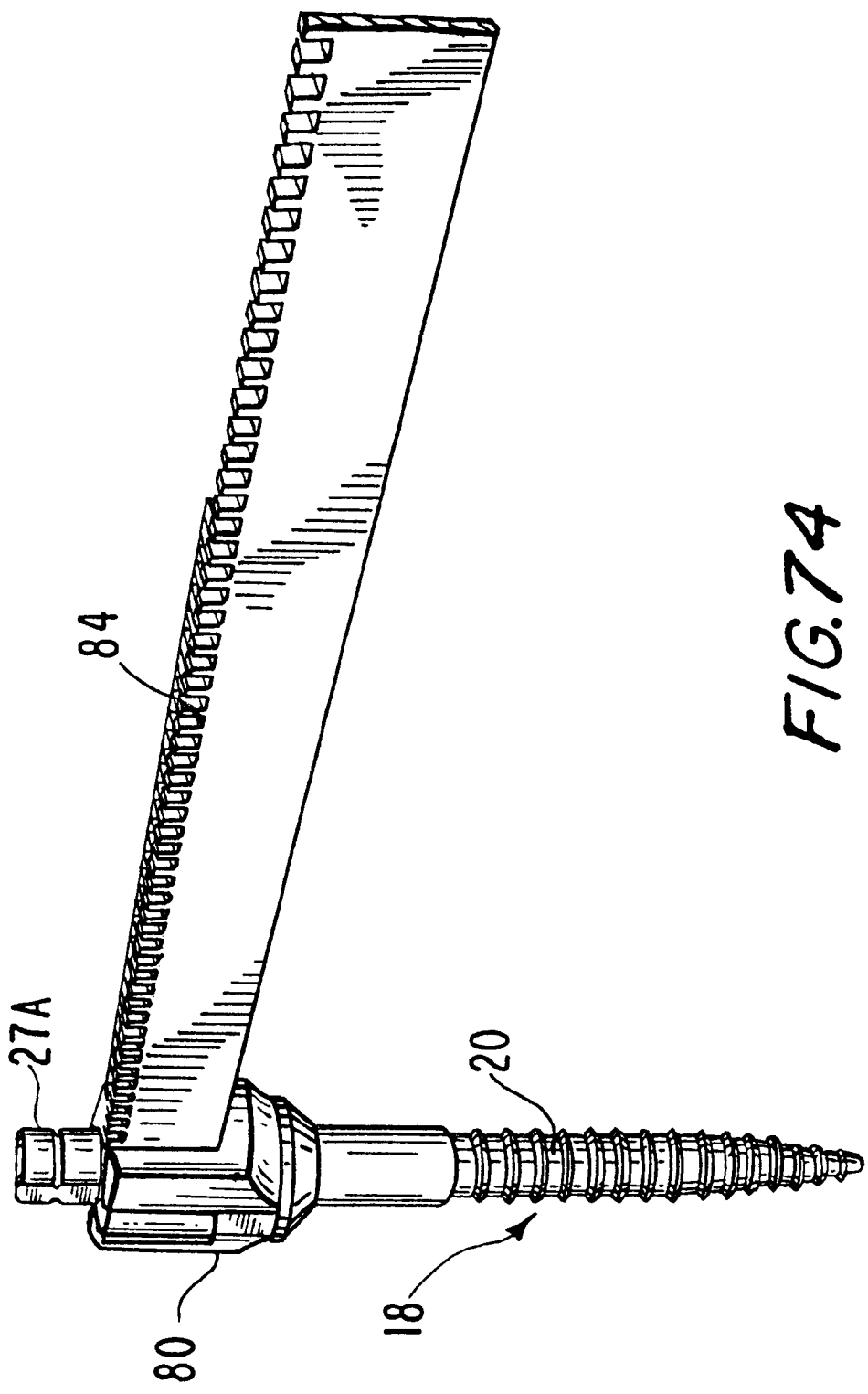
FIG. 74 illustrates a perspective view of the combination shown in FIG. 72.

FIGS. 72–74 illustrate various views of the end bar 84 of FIGS. 69–71 in combination with a screw 18, cap 27, and bucket-shaped indexing member 80 of FIGS. 55–61.

Figure 75:
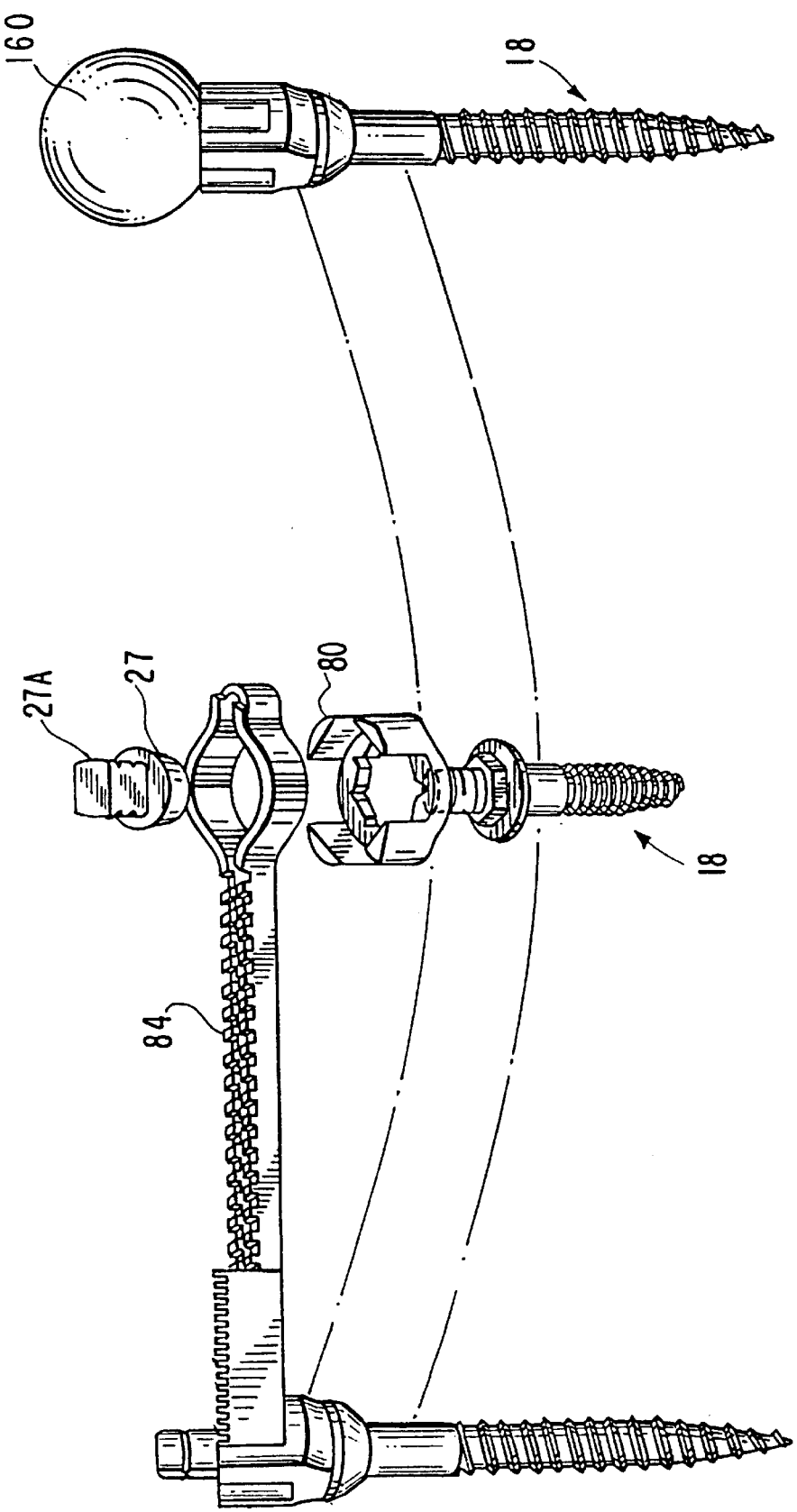
FIG. 75 illustrates an alternative embodiment of the combinations of FIGS. 72–74, including a ball-shaped cap.

FIG. 75 illustrates an alternative embodiment of the combinations of FIGS. 72–74, including a ball-shaped cap 160, with the ball-shape of the cap 160 useful to facilitate the removability of an overlying denture having a complementary socket, as described with reference to FIG. 83. The ball-shaped cap 160 may be a separate unit, or may be a ball-shaped extension integrally formed with the cap 27, or alternatively can be a separate attachment to the cap 27, fitting over and being permanently or removably secured to the extension 27A. The ball-shaped cap 160 may include a slot 162 which permits a dentist to turn the ball cap 160 and, if present, the underlying cap 27, using an appropriate tool such as a screwdriver, and so to insert or remove the ball 160 and/or the cap 27 with the ball, from the prosthetic connecting member 26 of the screw 18. Also see FIGS. 88–91.

Figure 76:
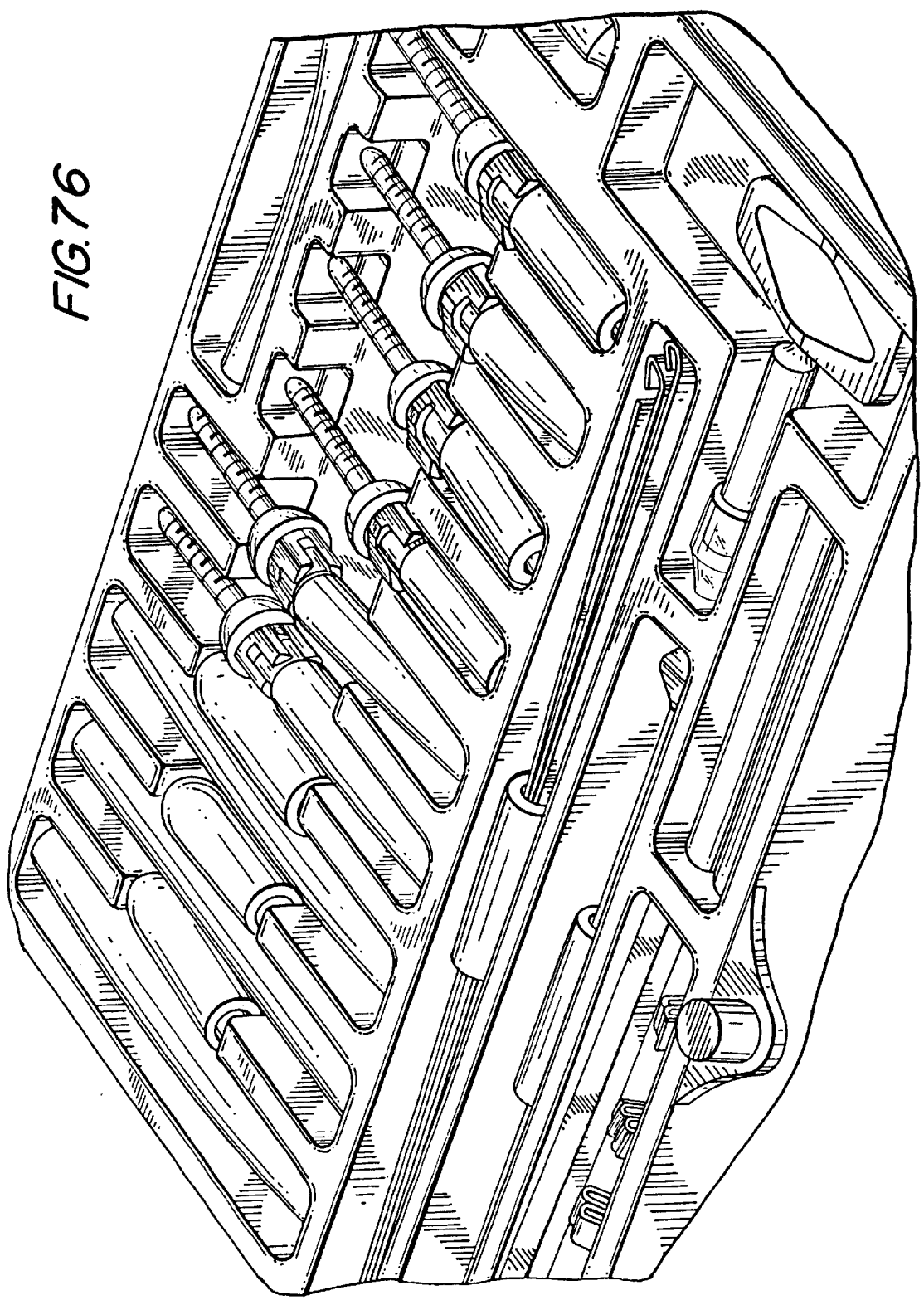
FIG. 76 illustrates a perspective view of a kit including various sizes of modular components of FIGS. 2–75.
Figure 77:
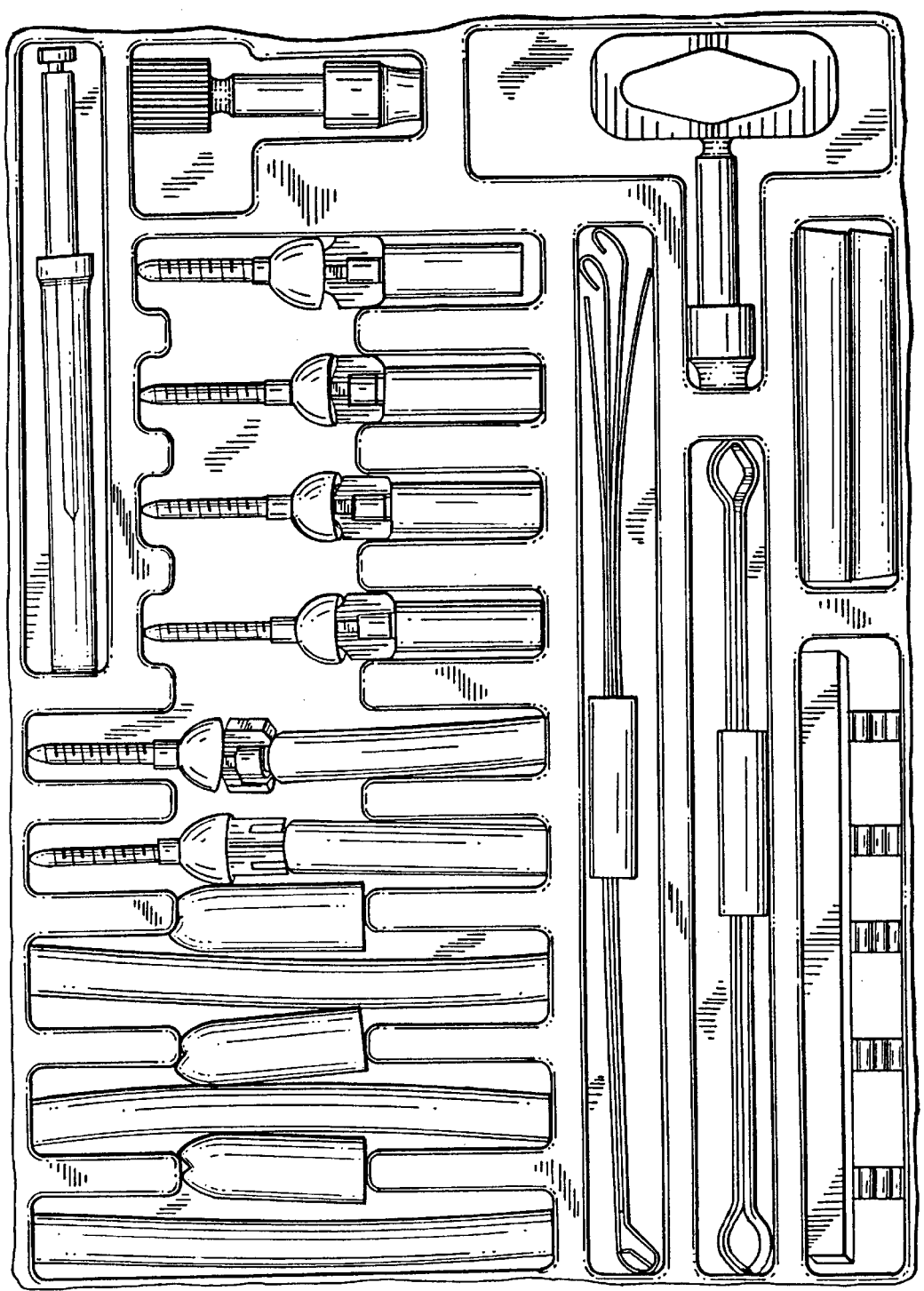
FIG. 77 illustrates a top plan view of the kit of FIG. 76 including various sizes of modular components of FIGS. 2–75.

FIGS. 76–77 illustrate various views of a kit including various sizes of modular components of FIGS. 2–83, which provides a dental technician with a chair-side variety of components for immediate application to construct and form a foundation in a patient's mount for subsequent preparation of a denture for the patient.

FIG. 78 illustrates a mold or form 102 for use in forming resin 104 into a solidified foundation about a split 10, with the mold 102, having unhardened resin 104 and holes 106 therethrough to prevent air bubbles in the formed foundation, being applied about the split 10 mounted to the plurality of implant screws 18, as shown in FIG. 20. In an alternative embodiment, the mold 102 can be flexible to allow a dentist readily adapt the mold 102 and the foundation to be formed to any dimensions and sizes of the jaw 14 of the patient.

In another alternative embodiment, the mold 102 can be filled with tooth-colored acrylic as the resin 104, to allow a dentist to form an instant prosthesis having the appearance of whitened teeth.

FIGS. 79–80 and 86–87 illustrate use of the expander clip 140 of FIGS. 49–50 for spacing bars 90, 92 apart, for receiving the foundation-forming resin therebetween, for example, from the mold 102 in FIG. 78. FIG. 80 shows a top cross-sectional view of the spaced apart bars of FIG. 79, in which a space 141 is formed between the bars 90, 92 for receiving the resin 104 from the mold 102.

FIGS. 81–82 and 86–87 also illustrate use of the spacer clip 150 of FIGS. 51–54 for spacing bars 90, 92 apart, for receiving the foundation-forming resin 104 therebetween, for example, from the mold 102 in FIG. 78. FIG. 82 shows a bottom cross-sectional view of the spaced apart bars 90, 92 of FIG. 81, in which a space 151 is formed between the bars 90, 92 for receiving the resin 104 from the mold 102.

It is believed that by separating the connecting bars 90, 92, so as to permit the resin to flow into and harden between them, the interlocking system is made even stronger and more rigid, much in the way of reinforcing cement.

FIG. 83 illustrates the ball-and-socket arrangement for use with the ball cap 160 of FIG. 75. At least one socket 164 is attached to the underside of the denture 62, such that complementarily-positioned ball caps 160, disposed on respective screws 18 distributed along the spilt 10 forming the foundation above the tissue 64, respectively engaging the at least one socket 164 in a removable configuration of ball-in-socket for a secure fit, with the denture 62 being readily removable from the split 10 by applying sufficient force to remove the sockets 164 from their respective ball portions on the ball caps 160. The smooth surfaces of the ball portions of the ball caps 160 permit more effective cleaning when the denture 62 is removed.

Figure 84:
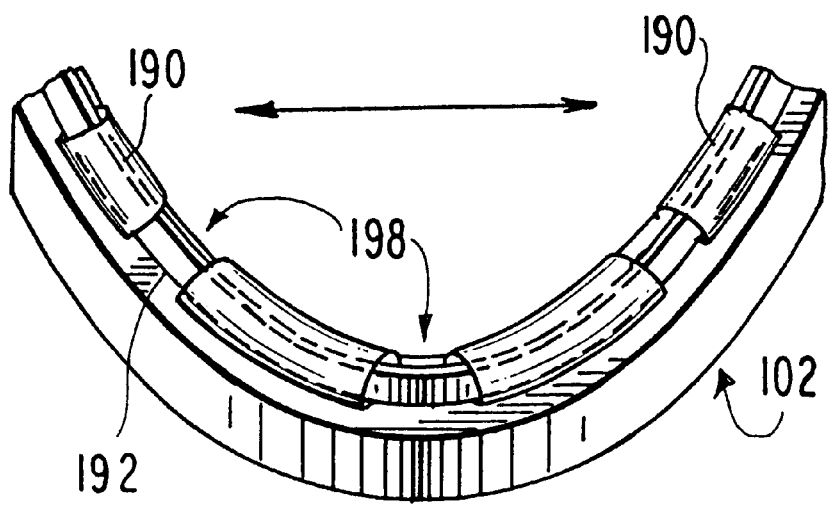
FIG. 84 illustrates a top perspective view of an alternative embodiment of a resin mold with a bar extending therethrough.
Figure 85:
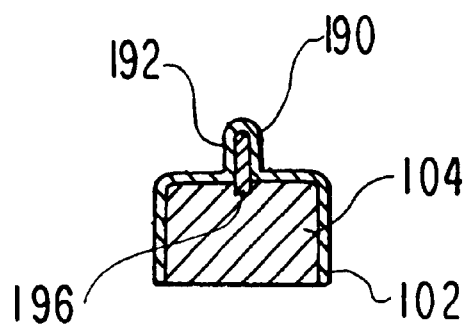
FIG. 85 illustrates a cross-sectional view of the mold of FIG. 84.
Figure 86:
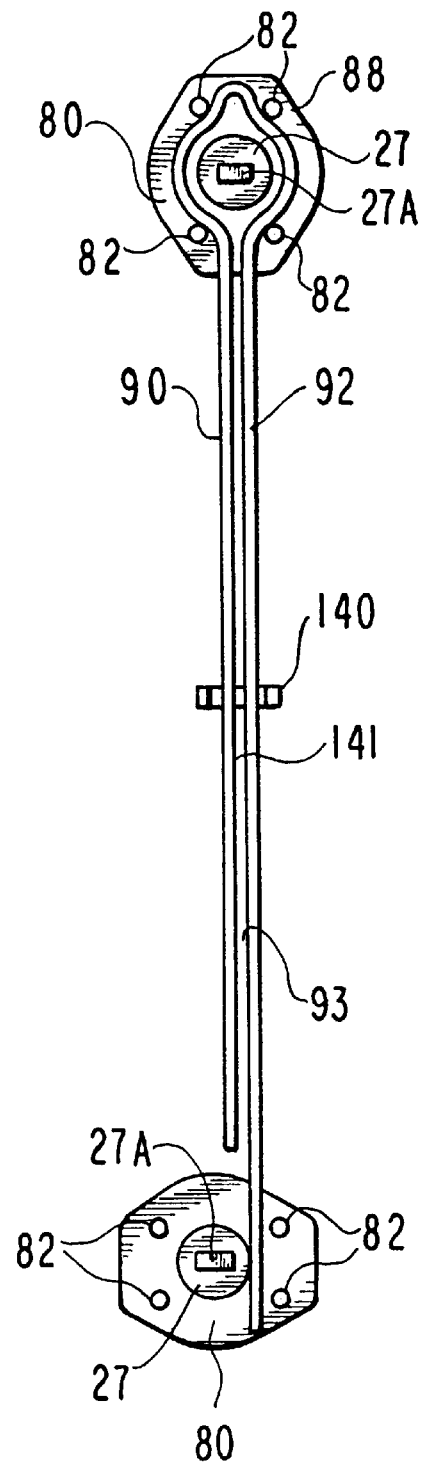
FIG. 86 illustrates a top plan view of the expander clip of FIGS. 49–50 providing a gap between intermediate portions of bars mounted between a pair of caps shown in FIG. 15, and held in place by the posts of an implant platform shown in FIG. 55.
Figure 87:
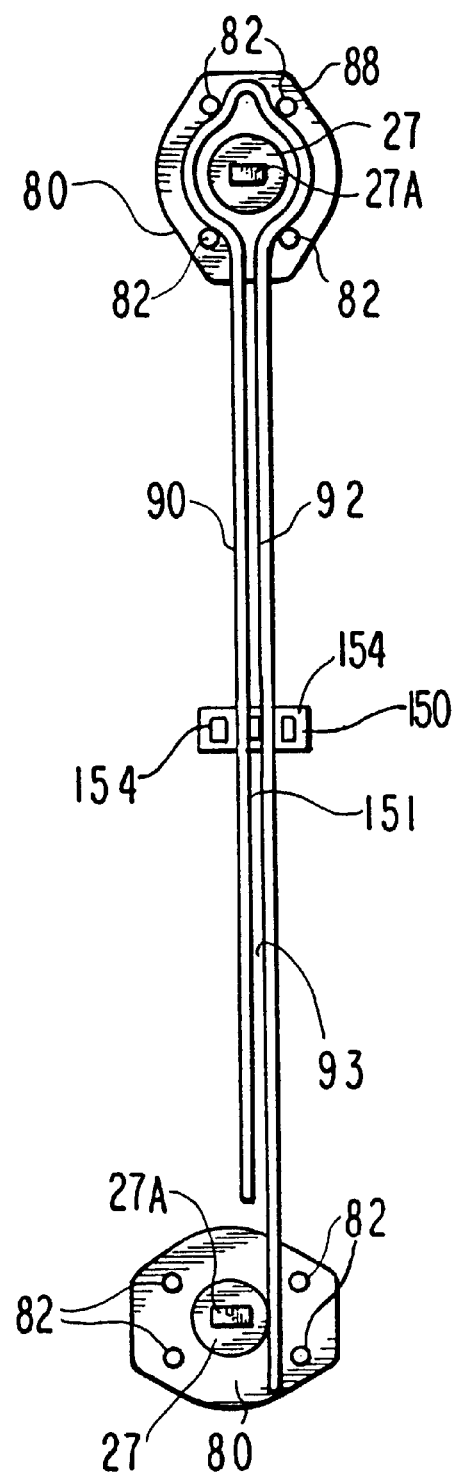
FIG. 87 illustrates a top plan view of the spacer clip of FIGS. 51–52, with a slotted portion in phantom, providing a gap between intermediate portions of bars mounted between a pair of caps shown in FIG. 15, and held in place by the posts of an implant platform shown in FIG. 55.
Figure 88:
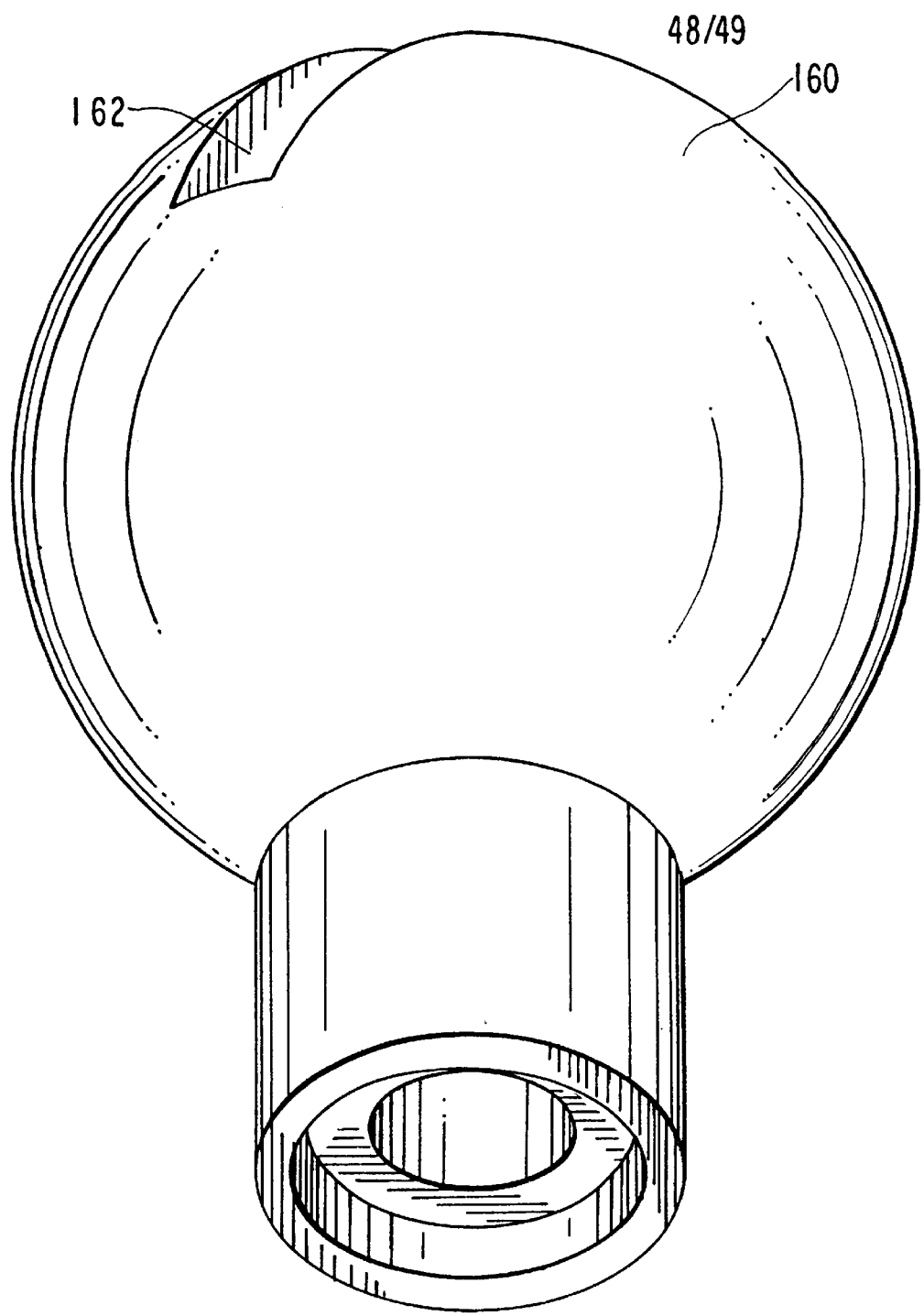
FIG. 88 illustrates an engineering drawing of a perspective view of the ball-shaped cap of FIGS. 75 and 83.
Figure 89:
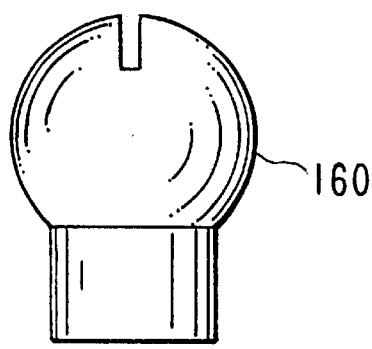
FIG. 89 illustrates a side plan view of the ball-shaped cap of FIGS. 75 and 83 and 88.
Figure 90:
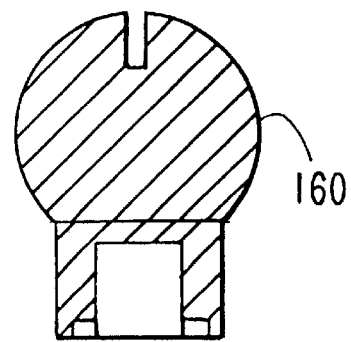
FIG. 90 illustrates a side cross-sectional view of the ball-shaped cap of FIGS. 75 and 83 and 88.
Figure 91:
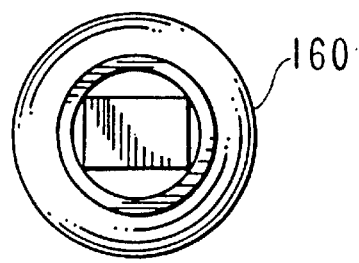
FIG. 91 illustrates a bottom plan view of the ball-shaped cap of FIGS. 75 and 83 and 88, having a polygonally shaped aperture for engaging the prosthesis connecting member of the implant screw of FIG. 2.

Referring to FIGS. 84–85 in conjunction with FIG. 78, an alternative embodiment of the mold 102 may include a pocket 190 along the length of the mold 102, or alternatively a plurality of pockets 190, as in FIG. 84. Each pocket 190 is positioned at the top of the mold 102, which allows a bar 192 to be run throughout the length of the mold 102 above the resin 104, with a portion 196 of the bar 192 extending in the resin 104. Gaps 198 between the pockets 190 facilitate the running of the bar 192 along the length of the mold 102. The bar 192 may be a thin length of metal, such as titanium, which hardens into the top of the resin 104, and thus runs along the length and the top of the formed splint 10.

After hardening of the resin 104, the mold 102 is removed, and if necessary is cut away from the bar 192. The bar 192 may thus form an integral track upon which to fit the overlying bridge or denture 62, as in FIG. 20. In addition, the bar 192 facilitates the formation of curves in the splint 10 for matching the curve of the upper and lower jaws.

While there has been shown the fundamental novel features of the invention as applied to the preferred embodiment, as is presently contemplated for carrying it out, it is to be understood that various omissions, substitutions, and changes of the form and details of the invention illustrated and described herein and in its use and operation may be made by those skilled in the art, without departing from the spirit of the invention.

What is claimed is:

1. A foundation of a rigid prosthetic dental bridge, which can be formed in situ in the mouth of a patient, said foundation comprising:
   at least two modules, each module comprising at least one of:
   (a) a shaft;
   (b) a longitudinal connecting bar,
   (c) an indexing extension unit; and
   (d) a locking cap for releasably securing the indexing extension unit to the shaft,
   the shaft comprising;
      a threaded portion at a first end adapted to anchor the shaft into rigid dental material selected from the group consisting of tooth stubs and bone matrix; and
      a multi-faceted driving/retaining portion at the second end of the shaft for connecting to a driving tool for driving the screw end into the rigid dental material and for engaging the extension unit after the shaft is anchored into the rigid dental material,
   the longitudinal connecting bar extending longitudinally transversely to the shaft; and
   said indexing extension unit comprising:
      (i) a base portion having an outer circumferential surface and a multi-faceted internal circumferential surface, and end surfaces extending transversely to the outer and internal circumferential surfaces, the multi-faceted internal surface at least partially defining a central aperture extending through the base portion, the shaft extending through the central aperture so that the multi-faceted driving/retaining portion of the shaft engages the multi-faceted internal circumferential surface of the extension unit, and thus releasably but nonrotatably engaging the second retaining/driving portion of the shaft in any of a plurality of desired angular juxtapositions; and
      (ii) at least one pair of arms extending from said base, each from a location spaced radially outwardly from the internal circumferential surface, and forming a slot therebetween, for engaging and supporting one end of the connecting bar, the connecting bar also engaging and being supported by the indexing extension unit of a second module; the connecting bar being sufficiently flexible to form a closed loop around at least one arm of at least one extension unit;
   the multi-faceted internal circumferential surface permitting the nonrotatable engaging of the retaining end in different angular juxtapositions so as to orient the slot in a desired direction; each extension unit being releasably secured to the shaft by the locking cap, which acts without interfering with the connecting bar or the arms;
   wherein the rigid prosthetic dental bridge foundation is formed which can be supported on and removably secured to the combination of at least two shafts.

2. The foundation of claim 1, comprising two pairs of arms thereby forming an extension unit with more than one slot.

3. The foundation of claim 1 further comprising dental resin encasing each indexing extension unit and the connecting bar, to form a unitary rigid foundation, the indexing unit and connecting bar serving as reinforcements for the resin.

4. The foundation of claim 1 wherein the locking cap further comprises an extension axially longitudinally extending outwardly from the cap distal the shaft.

5. The foundation of claim 4 further comprising a sleeve surrounding each locking cap and the cap extension, the sleeve being formed of a material non-adherent to the encasing dental resin, whereby the locking cap can be removed, freeing the unitary rigid foundation to be removed from the shafts.

6. The foundation of claim 5 wherein the sleeve is formed of a silicone resin.

7. A substantially rigid, removable foundation for a dental prosthesis which can be formed in situ in the mouth of a patient, the foundation comprising:

a longitudinal connecting bar;

a plurality of shafts interlocked with the connecting bar; and at least one extension unit rigidly holding at least one of the plurality of shafts and the connecting bar together, the extension unit includes:
- a mounting portion with an aperture therethrough to removably engage a respective second retaining end; and
- a side portion with at least a pair of arms forming at least one slot therebetween to engage and hold portions of other modules the extension unit thus having at least one slot through which the connecting bar is disposed, the rigid structure being constructed to be supported by the combination of the longitudinal connecting bar, the extension unit, and the plurality of shafts anchored to rigid dental material, the longitudinal connecting bar extending along and through the slots in the at least one extension unit, so that the rigid foundation can be readily removed from and replaced onto the implanted shafts, and artificial teeth can be secured thereto.

8. The foundation of claim 7 further comprising a locking cap secured to the shaft so as to lock the extension unit and the connecting member to the respective shaft.

9. The foundation of claim 8 wherein the locking cap further comprises a ball at the end distal from the shaft.

10. The foundation of claim 8 wherein the locking cap further comprises an extension longitudinally extending from the cap away from the shaft.

11. The foundation of claim 10 further comprising a sleeve surrounding the cap extension, the sleeve being formed of a material non-adherent to the dental resin used for forming a dental prosthesis.

12. The foundation of claim 11 wherein the sleeve is formed of a silicone resin.

13. The foundation of claim 8 further comprising an encasing resin encasing the foundation, wherein the connecting bars serve as reinforcements for the resin, but wherein the locking cap is not fully encapsulated by the resin.

* * * * *